(12) United States Patent
Yu

(10) Patent No.: US 11,766,361 B2
(45) Date of Patent: Sep. 26, 2023

(54) PRESSURE BANDAGE

(71) Applicant: Andrew S. Yu, New York, NY (US)

(72) Inventor: Andrew S. Yu, New York, NY (US)

( * ) Notice: Subject to any disclaimer, the term of this patent is extended or adjusted under 35 U.S.C. 154(b) by 300 days.

(21) Appl. No.: 16/249,375

(22) Filed: Jan. 16, 2019

(65) Prior Publication Data

US 2019/0216650 A1    Jul. 18, 2019

Related U.S. Application Data

(60) Provisional application No. 62/618,072, filed on Jan. 16, 2018.

(51) Int. Cl.
*A61F 13/00* (2006.01)
*A61F 13/14* (2006.01)
(Continued)

(52) U.S. Cl.
CPC .......... *A61F 13/00* (2013.01); *A61F 13/0226* (2013.01); *A61F 13/143* (2013.01);
(Continued)

(58) Field of Classification Search
CPC .... A61F 2013/00468; A61F 2013/0028; A61F 2013/00089; A61F 2013/00106; A61F 2013/00463; A61F 2013/00365; A61F 2013/00361; A61F 2013/00119; A61F 2013/49071; A61F 2013/00544; A61F 2013/00655; A61F 13/00; A61F 13/02; A61F 13/0203; A61F 13/0276; A61F 13/00051; A61F 13/00068; A61F 13/14; A61F 13/146; A61F 13/143; A61F 13/0226; A61F 13/148; A61F 17/00; A61F 5/30;
(Continued)

(56) References Cited

U.S. PATENT DOCUMENTS 2,560,712 A    7/1951    Bell
3,613,679 A    10/1971   Bijou
(Continued)

FOREIGN PATENT DOCUMENTS

CN          2766801 Y      3/2006
DE       202014002947 U1   5/2014
(Continued)

OTHER PUBLICATIONS

International Search Report and Written Opinion dated May 13, 2019 for Application No. PCT/US2019/13797.
(Continued)

*Primary Examiner* — Caitlin A Carreiro
(74) *Attorney, Agent, or Firm* — Plumsea Law Group, LLC

(57) ABSTRACT

A pressure bandage including an elastic sheet having a first coefficient of elasticity and an adhesive side. The pressure bandage may also include a resilient pad having a second coefficient of elasticity and affixed to the adhesive side of the elastic sheet. The elastic sheet has a first predetermined shape that is configured to be applied to a corresponding anatomical location on the body of a patient. The first coefficient of elasticity and the second coefficient of elasticity are related such that, when the elastic sheet is stretched and adhered to the body of the patient, the resilient pad applies a predetermined amount of pressure to the body of the patient.

8 Claims, 22 Drawing Sheets

(51) Int. Cl.
*A61N 1/372* (2006.01)
*A61M 31/00* (2006.01)
*A61F 13/02* (2006.01)

(52) U.S. Cl.
CPC .......... *A61F 13/148* (2013.01); *A61M 31/002* (2013.01); *A61N 1/372* (2013.01); *A61F 2013/00468* (2013.01); *A61F 2013/00544* (2013.01); *A61F 2013/00655* (2013.01)

(58) Field of Classification Search
CPC .......... A61F 5/443; A61F 5/44; A61F 5/4404; A61F 5/03; A61F 5/32; A61F 13/00008; A61F 13/00021; A61F 13/0243; A61F 13/0246; A61F 13/0253; A61F 13/069; A61F 13/06; A61F 13/063; A61F 2013/00582; A61F 13/061; A61F 13/023; A61F 13/00085; A61F 13/0259; A61F 13/60; A61F 2/0009; A61M 31/002; A61N 1/372; A61K 9/7038; A61L 15/16; A61L 15/42; A61L 15/58
USPC ............. 602/41–43, 53, 54, 58, 52, 57; 128/887–894; 424/445, 449, 448; 604/304, 307; 606/201
See application file for complete search history.

(56) References Cited

U.S. PATENT DOCUMENTS

| | | | |
|---|---|---|---|
| 4,212,296 A | 7/1980 | Schaar | |
| 4,224,945 A | 9/1980 | Cohen | |
| 4,719,909 A | 1/1988 | Micchia et al. | |
| 4,793,003 A | 12/1988 | Riedel et al. | |
| 4,971,046 A * | 11/1990 | Simpson | A61F 13/0203 602/57 |
| 5,195,950 A | 3/1993 | Delannoy | |
| 5,235,975 A | 8/1993 | Gang et al. | |
| 5,263,966 A | 11/1993 | Daneshvar | |
| 5,376,067 A | 12/1994 | Daneshvar | |
| D355,489 S | 2/1995 | Almond | |
| 5,464,420 A | 11/1995 | Hori et al. | |
| 5,514,155 A | 5/1996 | Daneshvar | |
| 5,538,500 A | 7/1996 | Peterson | |
| 5,643,315 A | 7/1997 | Daneshvar | |
| 5,690,610 A | 11/1997 | Ito et al. | |
| 5,779,657 A * | 7/1998 | Daneshvar | A61B 17/135 602/60 |
| 5,779,659 A | 7/1998 | Allen | |
| 5,891,074 A | 4/1999 | Cesarczyk | |
| 5,944,017 A | 8/1999 | Tweedle | |
| 6,164,279 A | 12/2000 | Tweedle | |
| 6,264,976 B1 | 7/2001 | Heinecke et al. | |
| D446,913 S | 8/2001 | Holden | |
| D455,002 S | 4/2002 | Holden | |
| 6,384,294 B1 | 5/2002 | Levin | |
| D463,564 S | 9/2002 | Siegwart et al. | |
| 6,573,419 B2 | 6/2003 | Naimer | |
| D498,841 S | 11/2004 | Bell et al. | |
| 6,812,375 B2 | 11/2004 | Dennis et al. | |
| 6,932,785 B1 | 8/2005 | Shesol | |
| 6,998,510 B2 | 2/2006 | Buckman et al. | |
| D516,727 S | 3/2006 | Neri | |
| 7,011,401 B2 | 3/2006 | Markey, III | |
| D518,892 S | 4/2006 | Hantke et al. | |
| 7,135,606 B1 * | 11/2006 | Dozier | A61F 13/0203 602/56 |
| 7,329,792 B2 | 2/2008 | Buckman et al. | |
| 7,507,870 B2 | 3/2009 | Nielsen et al. | |
| D608,453 S | 1/2010 | Arbesman et al. | |
| D618,474 S | 6/2010 | Maddadi | |
| D620,123 S | 7/2010 | Igwebuike | |
| 7,927,295 B2 | 4/2011 | Bates et al. | |
| 7,943,810 B2 | 5/2011 | Buckman et al. | |
| 8,034,009 B2 | 10/2011 | Bates et al. | |
| 8,252,970 B2 | 8/2012 | Buckman et al. | |
| 8,357,831 B2 | 1/2013 | Buckman et al. | |
| D705,429 S | 5/2014 | Cheney et al. | |
| 8,759,602 B2 | 6/2014 | Buckman et al. | |
| D748,276 S * | 1/2016 | Bergström | D24/189 |
| D785,189 S | 4/2017 | Dettmar | |
| D787,688 S | 5/2017 | Stephenson | |
| 9,789,006 B2 | 10/2017 | Joyner | |
| D811,610 S | 2/2018 | Abel et al. | |
| D863,577 S | 10/2019 | Chobuathong | |
| D868,267 S | 11/2019 | Del Rossi et al. | |
| D875,958 S | 2/2020 | Emslander et al. | |
| D876,640 S | 2/2020 | King | |
| 2004/0049146 A1 * | 3/2004 | Kolte | A61F 13/0203 602/61 |
| 2008/0319473 A1 | 12/2008 | Rosenbaum | |
| 2009/0112141 A1 | 4/2009 | Derr | |
| 2009/0187212 A1 * | 7/2009 | Matsui | A45D 44/22 606/201 |
| 2011/0237994 A1 | 9/2011 | Russ et al. | |
| 2012/0029406 A1 | 2/2012 | Bates et al. | |
| 2012/0130297 A1 | 5/2012 | Loescher et al. | |
| 2012/0175370 A1 * | 7/2012 | Walunis | B65D 51/221 220/258.1 |
| 2012/0189796 A1 * | 7/2012 | Aoyagi | A61K 9/703 428/41.8 |
| 2012/0232578 A1 | 9/2012 | Altobelli et al. | |
| 2014/0228732 A1 | 8/2014 | Steinbaugh et al. | |
| 2015/0290455 A1 | 10/2015 | Bornzin et al. | |
| 2016/0095755 A1 | 4/2016 | Joyner | |
| 2016/0199230 A1 * | 7/2016 | Doshi | A61F 13/58 156/219 |

FOREIGN PATENT DOCUMENTS

| | | | |
|---|---|---|---|
| EP | 0614652 A1 * | 9/1994 | ......... A61B 17/1325 |
| EP | 614652 A1 * | 9/1994 | ......... A61B 17/1325 |
| EP | 0614652 B1 | 7/2001 | |
| EP | 2708215 A1 | 3/2014 | |
| WO | 2017220401 A1 | 12/2017 | |

OTHER PUBLICATIONS

"How Much Pressure Does a Pressure Dressing Press? A Pilot Study Quantifying the Effects of a Pressure Dressing on the Post-Cesarean Section Incision", Wounds, 2006; vol. 18, No. 3, pp. 51-53.

* cited by examiner

PRESSURE BANDAGE

CROSS-REFERENCE TO RELATED APPLICATION(S)

This application claims priority to U.S. provisional application No. 62/618,072, filed Jan. 16, 2018, the disclosure of which is hereby incorporated by reference in its entirety.

BACKGROUND OF THE INVENTION

1. Field of the Invention

The present invention relates to pressure bandages and, more particularly, to pressure bandages configured for use in particular anatomic locations.

2. Description of Related Art

Different types of wound dressings serve various functions, including protecting the wound from trauma and contamination, reducing the risk of postoperative hematoma and seroma formation, providing compression of dead space, preventing heat and fluid loss, absorbing exudate, limiting wound disruption, and providing an aesthetically pleasing appearance. Since no single dressing exemplifies all of these attributes, the characteristics of a particular wound determine which of these functions are required of the dressing.

A "pressure dressing" is a dressing including a bulky component, such as a sponge or gauze pad, and at least one thin strip of material that may be applied to the body to press the bulky component against the wound site. The strip of material may include elastic or inelastic materials. When the strip of material is affixed to the patient, it is pulled tightly such that it forces the bulky component against the wound site. Application of a pressure dressing over a wound is intended to compress dead space and prevent hematoma and seroma formation. A pressure dressing can improve hemostasis by preventing capillary blood loss and exudate.

Pressure dressings may be applied to any type of wound, including trauma wounds, surgical wounds, or any other type of wound to which it is desirable to apply pressure. In some cases, pressure dressings are applied to medical device implantation surgical sites. For example, devices like pain pumps, pacemakers, and other devices are implanted in surgical "pockets" under the skin. Creating the surgical pocket is traumatic to the tissues surrounding the implanted device. Therefore a pressure dressing is used to minimize hematoma and seroma at the implantation site. Among other benefits, minimizing hematoma and seroma may promote healing and may also minimize the risk of infection. There is a need to prevent infection particularly in surgical pockets because a high percentage of pocket infections have poor outcomes.

To improve hemostasis, a pressure dressing may be used to at least partially collapse the capillary vessels in the subcutaneous tissues in order to allow platelet aggregation, plug formation, and formation of a fibrin clot. Similarly, exudate in subcutaneous tissue is determined by a combination of oncotic and hydrostatic pressure. Thus, pressure dressings may also be used to decrease seroma formation from exudate.

In many cases, pressure dressings are assembled in an ad-hoc fashion with multiple strips of tape, which may or may not be elastic, applied over a stack of gauze that has been centered on top of a wound. Thus, the clinician typically must tediously gather the components to construct a conventional pressure dressing and then assemble the dressing on the patient. For example, the clinician must pre-cut several strips of tape, place a stack of sponges, gauze, or other padding elements over the surgical pocket, and then apply the tape over the sponges while balancing the stack of sponges. If the clinician opts not to pre-cut the tape before the surgery, the process of applying the makeshift pressure dressing after the surgery can take even longer. Further, in some cases, the clinician applies additional tape strips to hold the ends of the initial tape strips down or they may use additional strips of tape to make the dressing pseudo-waterproof. Regardless of the chosen method for constructing and applying a makeshift dressing, the procedure is time consuming, cumbersome, and can be inconsistent with respect to the fit of the assembled dressing and the pressure applied by the dressing to the wound site.

The current practice of preparing makeshift pressure dressings is inefficient, as it is time-consuming, averaging 3-5 minutes to assemble and apply a conventional pressure dressing, and can sometimes require a second clinician's assistance. In addition, due to the custom-made nature of such dressings and the fact that different clinicians are constructing and applying the dressings from one procedure to another, there can be significant differences in the pressure the dressings apply to the wound sites. Also, these makeshift pressure dressings can be bulky and unprofessional in appearance, and can also be uncomfortable for the patient to wear and/or remove.

The disclosed devices address one or more of the issues noted above.

SUMMARY OF THE INVENTION

In order to address the shortcomings of makeshift pressure dressings discussed above, a pre-assembled pressure bandage is provided. The pre-assembled pressure bandage includes an elastic sheet having a predetermined shape and an adhesive side. The disclosed pressure bandage may also include a resilient pad affixed to the elastic sheet. The elasticity of the sheet and the resiliency of the pad cooperate to provide the desired amount of pressure when the disclosed pressure bandage is applied to the wound site.

In one aspect, the present disclosure is directed to a pressure bandage including an elastic sheet having a first coefficient of elasticity and an adhesive side. The pressure bandage may also include a resilient pad having a second coefficient of elasticity and affixed to the adhesive side of the elastic sheet. The elastic sheet has a first predetermined shape that is configured to be applied to a corresponding anatomical location on the body of a patient. The first coefficient of elasticity and the second coefficient of elasticity are related such that, when the elastic sheet is stretched and adhered to the body of the patient, the resilient pad applies a predetermined amount of pressure to the body of the patient.

In another aspect, the present disclosure is directed to a system including an implantable medical device configured to be implanted proximate the surface of the skin, and a pressure bandage. The pressure bandage may include an elastic sheet having an adhesive side and a resilient pad affixed to the adhesive side of the elastic sheet. The elastic sheet may have a first predetermined shape that is configured to be applied to a corresponding anatomical location on the body of a patient.

In another aspect, the present disclosure is directed to a method of applying a pressure bandage to a patient. The method may include applying a pressure bandage to a surgical site at an anatomical location of a patient, the surgical site including a surgically created pocket in which an implanted medical device is housed. Applying the pressure bandage to the patient applies a predetermined amount of pressure to the surgical site. The pressure bandage may include an elastic sheet having an adhesive side and a resilient pad affixed to the adhesive side of the elastic sheet. The elastic sheet may have a first predetermined shape that is configured to be applied to a corresponding anatomical location on the body of a patient. Applying the pressure bandage to the patient may include positioning the resilient pad against the skin of the patient over the location of the surgically created pocket.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
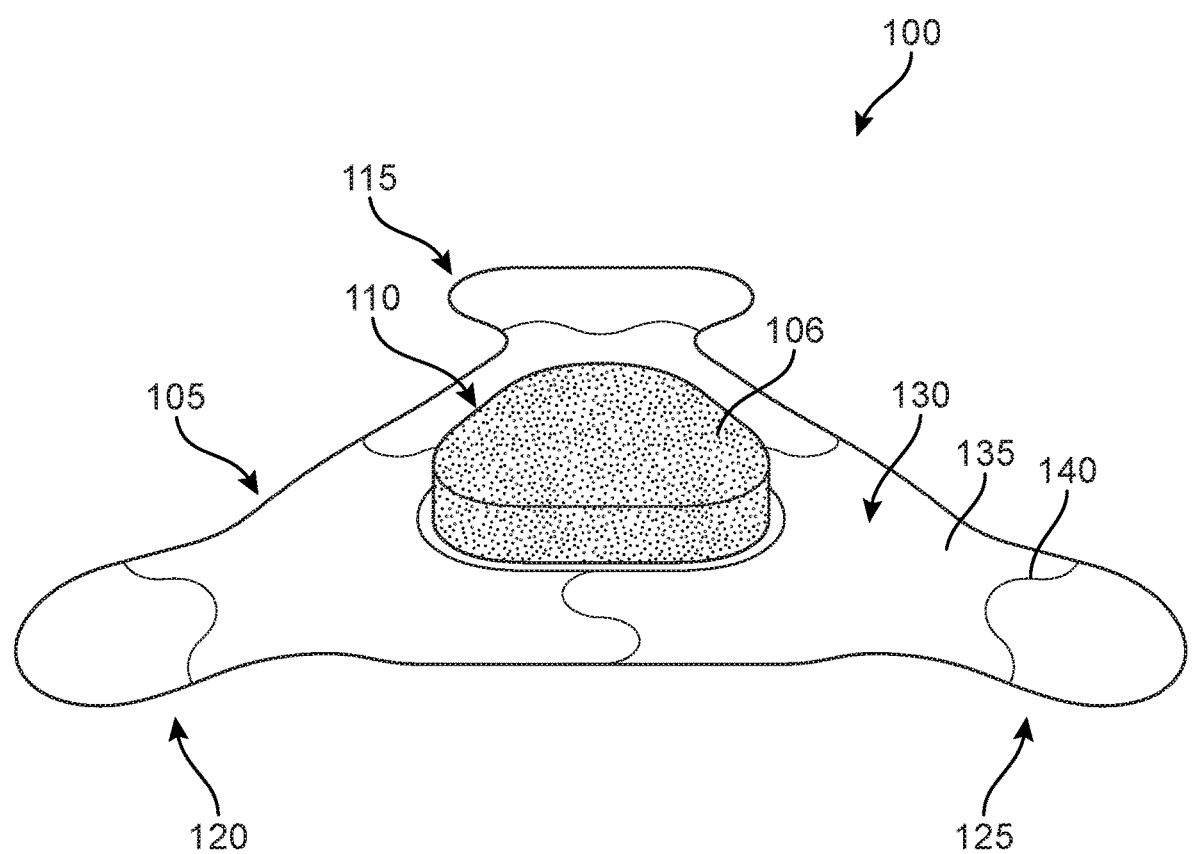
FIG. 1 is a schematic perspective view of a pressure bandage according to an exemplary disclosed embodiment.

There are several processes by which fluids may collect in the tissues of the body in the area of a wound site, whether the wound is incurred accidentally via trauma or purposefully, such as by a surgical procedure. For surgeries that involve the implantation of a device (e.g., subcutaneously), the pocket formed in the tissue to receive the device may provide a cavity in which the fluids can collect, causing pain and swelling.

Via one physiological mechanism, the surgical procedure can damage blood vessels in the tissue. If there are tears or other damage in the walls of the blood vessels, blood can directly escape into the surrounding tissues. This can result in hematoma at the surgical site. A hematoma is a collection of blood in dead space in the body. A hematoma, whether caused by trauma or surgery, can be caused by a small blood vessel being opened to the surrounding tissue. Hematomas may sometimes need to be drained because they can be painful, lead to scarring, and cause infection.

A seroma is a collection of fluid around a surgery site, caused by damage to the blood and lymph vessels and surrounding tissue. The body senses that damage has been done and produces an inflammatory response by flooding the area with a clear fluid.

Hemostasis is a process which causes bleeding to stop, meaning to keep blood within a damaged blood vessel (the opposite of hemostasis is hemorrhage). It is the first stage of wound healing. This involves coagulation, blood changing from a liquid to a gel. Intact blood vessels are central to moderating blood's tendency to form clots. The endothelial cells of intact vessels prevent blood clotting with a heparin-like molecule and thrombomodulin and prevent platelet aggregation with nitric oxide and prostacyclin. When endothelial injury occurs, the endothelial cells stop secretion of coagulation and aggregation inhibitors and instead secrete von Willebrand factor which initiate the maintenance of hemostasis after injury. Hemostasis has three major steps: 1) vasoconstriction, 2) temporary blockage of a break by a platelet plug, and 3) blood coagulation, or formation of a fibrin clot. These processes seal the hole until tissues are repaired.

To improve hemostasis, a pressure bandage may be used to at least partially collapse damaged blood vessels in the subcutaneous tissues in order to allow platelet aggregation, plug formation, and formation of a fibrin clot. This prevents blood or blood components from leaking out of the blood vessels and forming hematoma in the surrounding tissues. Similarly, exudate in subcutaneous tissue is also determined by a combination of oncotic and hydrostatic pressure. Thus, pressure bandages may also be used to decrease seroma formation from exudate.

In another physiological mechanism, due to the body's inflammatory response, the permeability of blood vessel walls increases, allowing fluids, proteins, and white blood cells (leukocytes) to escape through the vessel walls between the endothelial cells. These blood components form exudate that accumulates in the tissue at the surgical site. If this exudate is not prevented or readily managed, a seroma can form.

In order to prevent or minimize the collection of fluids, the present disclosure provides a pressure bandage configured to apply a predetermined amount of pressure to a wound site. The pressure bandage includes an elastic sheet having a first coefficient of elasticity and an adhesive side. The bandage also includes a resilient pad having a second coefficient of elasticity and affixed to the adhesive side of the elastic sheet. The first coefficient of elasticity and the second coefficient of elasticity are related such that, when the elastic sheet is stretched and adhered to the body of the patient, the resilient pad applies a predetermined amount of pressure to the body of the patient. The predetermined amount of pressure is in a range that prevents or minimizes the escape blood from damaged blood vessels and the passage of exudate through the walls of blood vessels, thereby preventing or minimizing the collection of fluids at the wound site.

FIG. 1 is a schematic perspective view of a pressure bandage according to an exemplary disclosed embodiment. FIG. 1 shows a pressure bandage 100, which may include an elastic sheet 105 and a resilient pad 110. In FIG. 1, the pressure bandage is upside down in order to show a skin contacting lower side 106 of resilient pad 110. As shown in FIG. 1, bandage 100 may have a substantially triangular shape, including a first anchor 115 at a first vertex of the triangular shape, a second anchor 120 at a second vertex of the triangular shape, and a third anchor 125 at a third vertex of the triangular shape.

In addition, elastic sheet 105 may have a skin contacting lower surface 135. Skin contacting lower surface 135 may include an adhesive configured to adhere to the skin of a patient. In order to facilitate storage and application of bandage 100, a liner 130 (e.g., release paper) may be affixed to the skin-contacting lower surface 135 (i.e. the adhesive side) of elastic sheet 105. In some embodiments, liner 130 may include a plurality of cut lines 140 separating liner 130 into distinct sections, wherein cut lines 140 are configured to facilitate removing the distinct sections of liner 130 in a predetermined sequence. The configuration of liner 130 and cut lines 140 is discussed in further detail below with respect to FIG. 7.

In some embodiments, elastic sheet 105 and/or resilient pad 110 of pressure bandage 100 may have a predetermined shape that is configured to be applied to a corresponding anatomical location on the body of a patient. For example, in some embodiments, pressure bandage 100 may be configured for application in an abdominal region, an upper chest region, a lumbar back region, an inguinal crease region, or any other region in which it would be desirable to apply a pressure bandage.

In some embodiments, pressure bandage 100 may be configured for application to a lower abdominal region of the patient. Further, in some cases, pressure bandage 100 may be configured for application to a surgical site in the lower abdominal region. Such a surgical site may include surgical wounds from procedures such as gastric surgeries, appendectomies, hernia surgeries, cesarean sections (C-sections), or subcutaneous device implantations.

Figure 2:
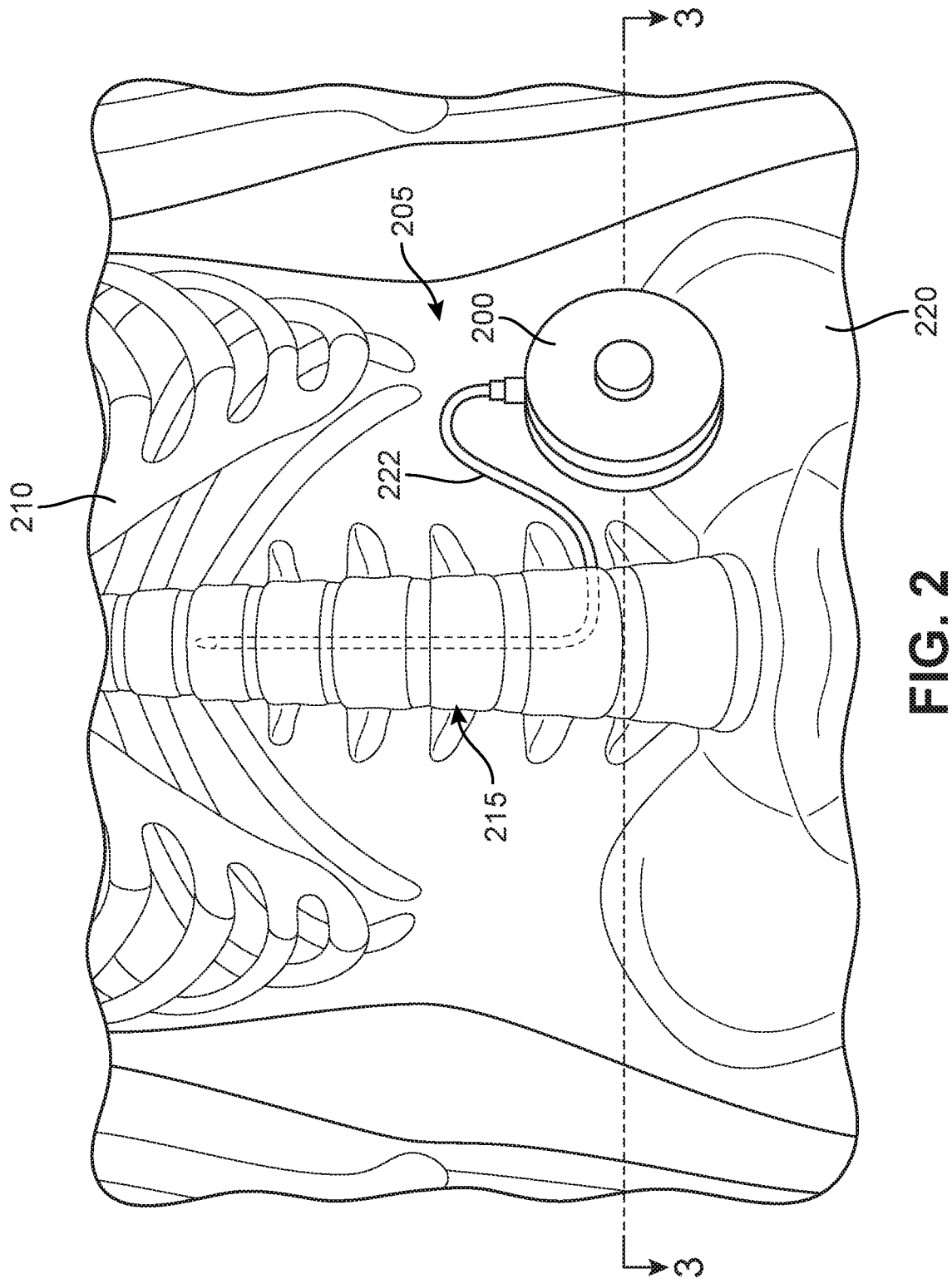
FIG. 2 is a schematic illustration of a medical device implanted in an abdomen of a patient.

In some embodiments, pressure bandage 100 may be configured for application to the site of a surgical pocket created for implantations of medical devices. FIG. 2 is a schematic illustration of a medical device 200 implanted in an abdomen 205 of a patient. As shown in FIG. 2, abdominal region 205 is defined, at least in part by a ribcage 210 located superior to abdominal region 205, a pelvis 220 located inferior to abdominal region 205, and a spinal column 215 located posterior to abdominal region 205.

The implantable medical device 200 may have one or more leads 222 extending from the main body of the implant and extending to nearby portions of the body. For example, as shown in FIG. 2, lead 222 may extend to spinal column 215. In some embodiments lead 222 may be a conduit configured to deliver a drug, such as pain medication to a part of the body, such as the cerebrospinal fluid. In such embodiments, medical device 200 may be a pump for delivering pain medication, and thus, may sometimes be referred to as a "pain pump." In other embodiments, lead 222 may include electrical leads configured for electrical stimulation. Such leads may be extended to muscles or nerves to provide electrical stimulation.

In other embodiments, different types of medical devices may be implanted in the lower abdominal region. Such devices may have different sizes or shapes. Such devices may be positioned to the left or right of the anatomical center of the body. For example, device 200 is shown in FIG. 2 as being implanted in the left side of the patient's abdomen. Pressure bandage 100 may be configured for application to the wound site for any of the various possible configurations of the implantable medical device.

In some embodiments, the medical device and pressure bandage may be part of a system wherein the two components are configured to work with one another. That is, the bandage may be sized and shaped to be applied to the particular anatomical area of the body in which the medical device is designed to be implanted. In addition, the resilient pad may be sized and shaped to cover an area substantially the same size and shape as the medical device. Thus, the resilient pad may be sized and shaped to substantially cover an area the size and shape as the surgical pocket into which the medical device is configured to be implanted.

Figure 3:
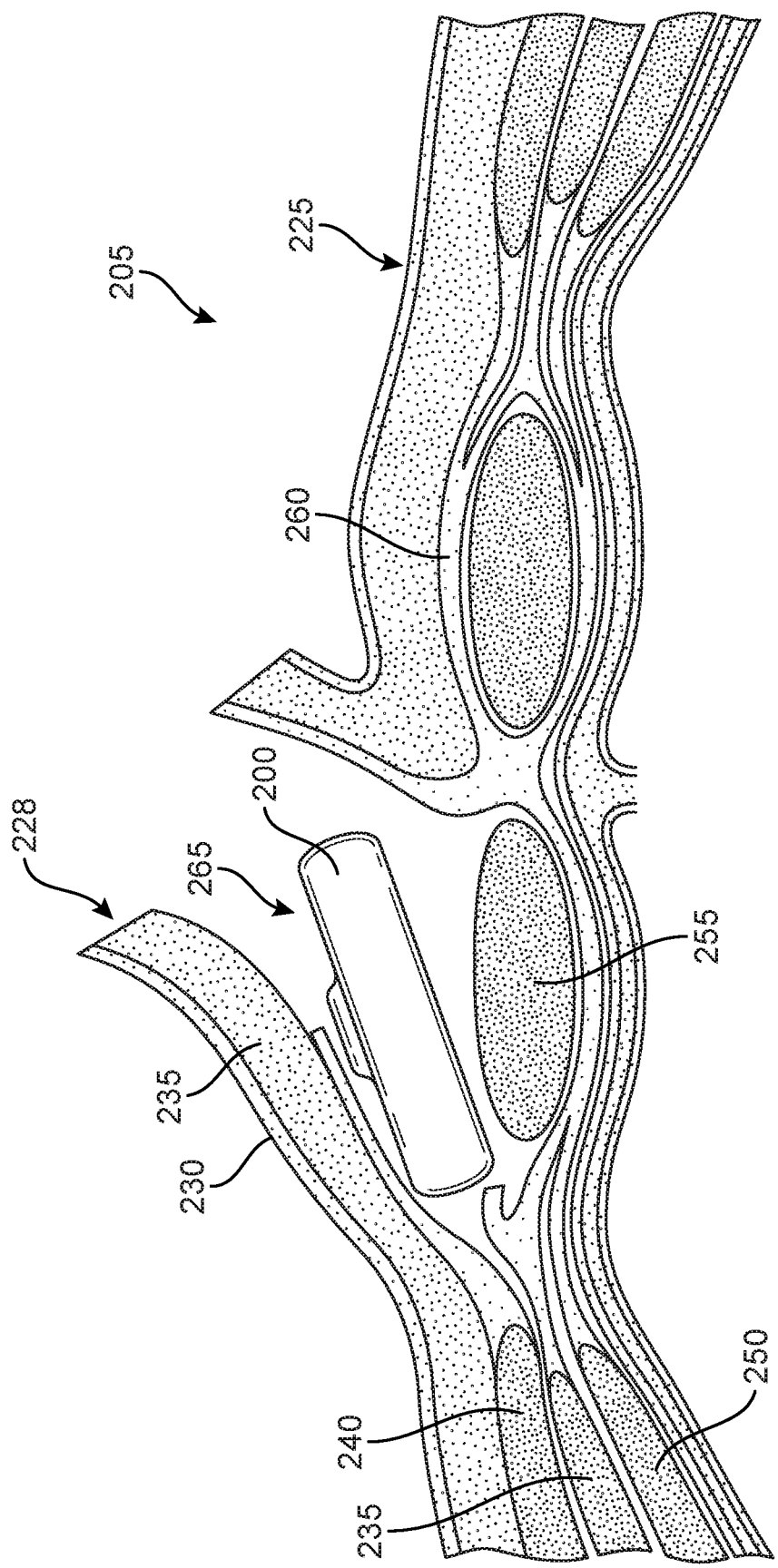
FIG. 3 is a schematic cross-sectional illustration of a subcutaneous abdominal implant and surgical pocket taken at line 3-3 in FIG. 2 in an inferior direction.

In some embodiments, the pressure bandage may be configured for application to surgical sites created by procedures involving the insertion of subcutaneous implants. FIG. 3 is a schematic cross-sectional illustration of a subcutaneous abdominal implant and surgical pocket taken at line 3-3 in FIG. 2. In particular, FIG. 3 shows implant 200 being inserted into a surgical pocket 265 in the abdominal region 205 of a patient through an outer surface 225 of the abdomen. FIG. 3 shows a flap 228 of tissue formed of skin 230 and subcutaneous tissue 235 under which implant 200 is being inserted. Flap 228 will be replaced over implant 200 and the incision closed. For reference, abdominal muscles and associated tissues are also shown in FIG. 2, including the external oblique 240, the internal oblique 245, the transverse abdominis 250, the rectus abdominis 255, and the rectus sheath 260.

Figure 4:
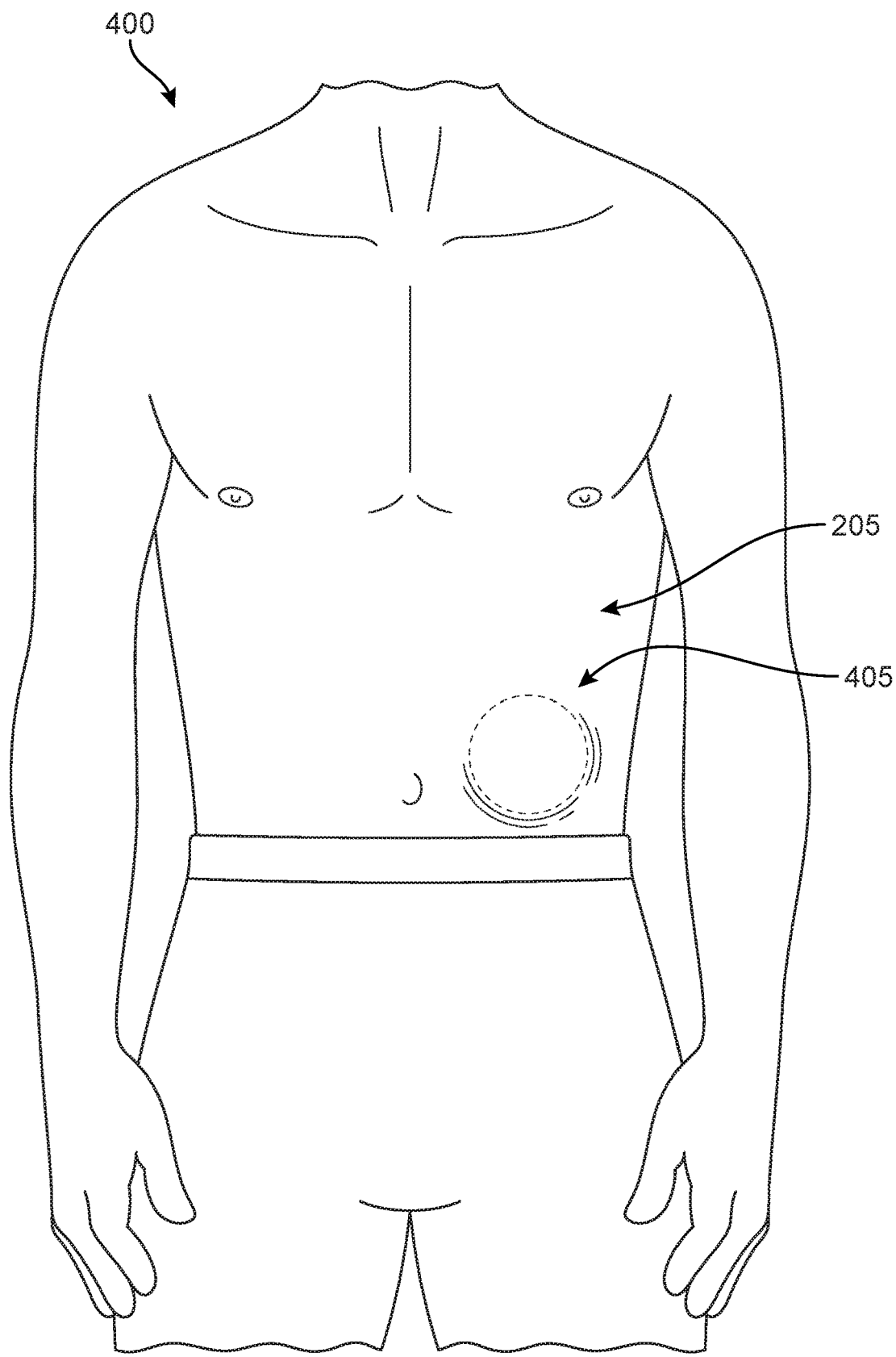
FIG. 4 is a schematic illustration of a patient with an abdominal bulge at an abdominal implant surgical site.
Figure 5:
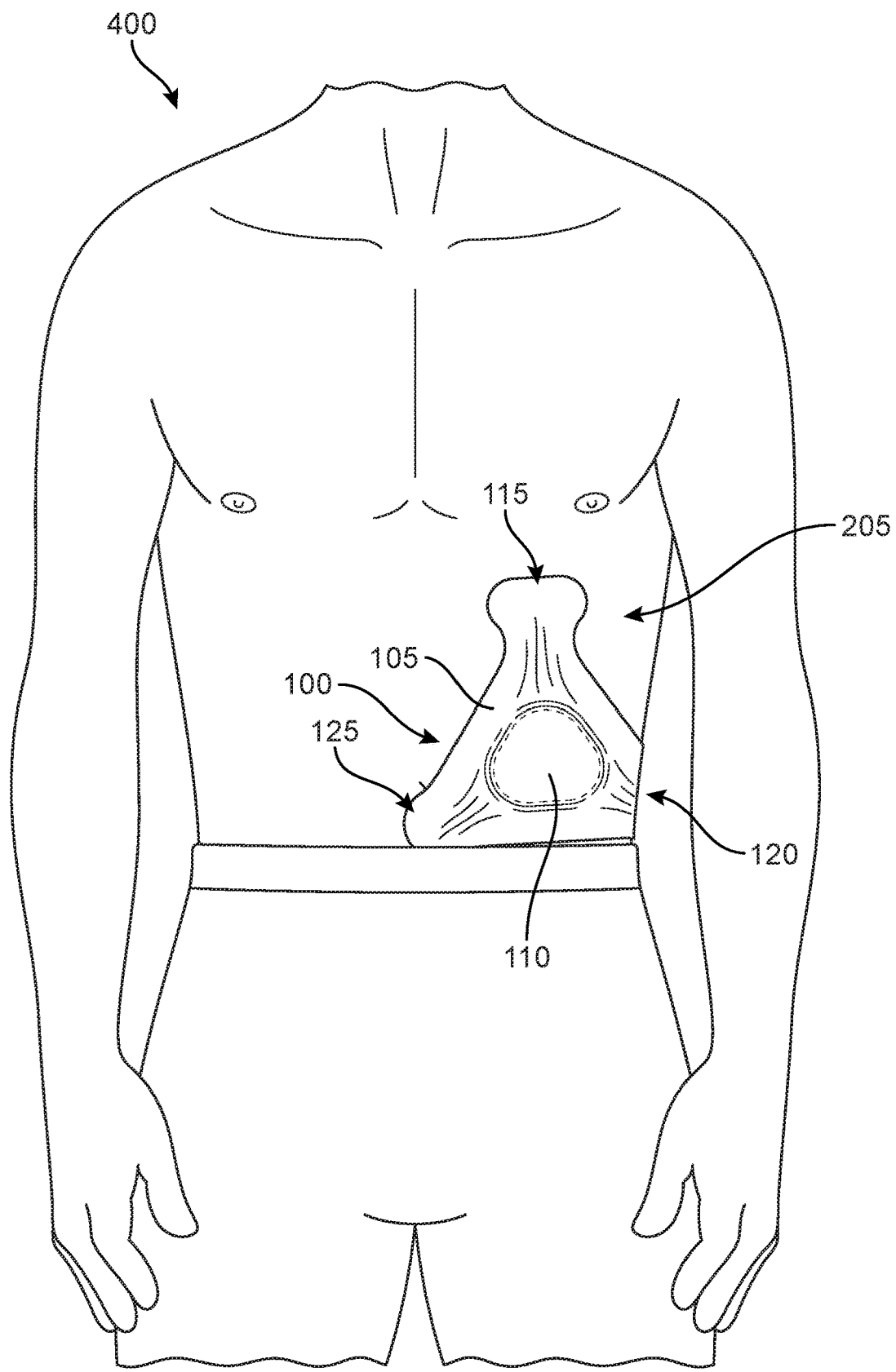
FIG. 5 is a schematic illustration of the patient shown in FIG. 4 with an exemplary pressure bandage applied to the abdominal surgical site.

In some cases, the implantable medical devices may have a thickness such that a bulge is created in the patient's tissues when the device is implanted. FIG. 4 is a schematic illustration of a patient 400 with an abdominal bulge 405 at an abdominal implant surgical site in abdominal region 205. FIG. 5 is a schematic illustration of the patient shown in FIG. 4 with an exemplary pressure bandage applied to the abdominal surgical site. As shown, pressure bandage 100 may be applied to the surgical site. First anchor 115 may be adhered in the upper portion of abdominal region 205. Second anchor 120 may be adhered around the patient's lateral torso, above the hip. In addition, third anchor 125 may be adhered across the central part of abdominal region 205. As shown in FIG. 5, pressure bandage 100 may be positioned so that resilient pad 110 may be located over the surgical pocket.

As illustrated in FIG. 5, elastic sheet 105 of pressure bandage 100 may be stretched firmly when pressure bandage 100 is applied to the body of patient 400. By pulling the anchors of pressure bandage 100 firmly when applying the bandage to the body, resilient pad 110 is pressed against the skin over the surgical pocket. The compressibility of resilient pad 110 enables resilient pad 100 to match the contours of the implanted medical device and the bulge in the abdomen created by the implanted device. Accordingly, resilient pad 110 is compressed against the skin by elastic sheet 105. Further, due to the resiliency of resilient pad 110, the compressed pad is biased to expand to its original, uncompressed condition. Accordingly, the compressed pad's bias to expansion applies pressure to the wound site.

The elasticity of elastic sheet 105 and the resiliency of resilient pad 110 may be configured to work in concert to produce a predetermined amount of pressure against the outer surface of the skin, and thus, produce a predetermined amount of pressure against the blood vessels of the tissues at the wound site. For example, elastic sheet 105 may have a first coefficient of elasticity and resilient pad 110 may have a second coefficient of elasticity. The first coefficient of elasticity and the second coefficient of elasticity may be related such that, when the elastic sheet is stretched and adhered to the body of the patient, the resilient pad applies a predetermined amount of pressure to the body of the patient.

Elastic sheet 105 may be formed of any suitable elastic sheet material. For example, in some embodiments, elastic sheet 105 may be formed of 3M™ Tan Hi Tack Nonwoven Medical Tape, product number 9904. This material is an elastic nonwoven tape with a tan polyurethane nonwoven backing and an acrylate adhesive developed for medical use. The liner or release paper is a silicone coated on both sides. The elongation in the machine direction (MD) is at least 300% minimum. The tensile break strength of this material, in the machine direction, is at least 4 lbs./inch of width.

Resilient pad 110 may be formed of any suitable resilient material. For example, in some embodiments, resilient pad 110 may be formed of viscoelastic foam, such as product number 6032 by Bergad, Inc. This material has an indentation forced deflection of 52 lb-ft. for 25% deflection. Compression set is less than 0.3% at 25% compression, and 0.5% at 50% compression. In some embodiments, product 6030 from Bergad, Inc. may be used. Product 6030 is another viscoelastic foam, but is more firm than product 6032. In particular, product 6030 has an indentation forced deflection of 68 lb-ft. for 25% deflection, compared to 52 lb-ft. for product 6032. The use of the softer foam may enable the pad to better conform to irregular shapes and/or edges of implants. When the implantable device has a sharp peripheral edge and/or when the bulge of the implanted device protrudes significantly, the softer pad may better conform around the form of the device, thus enabling pressure to be applied consistently across the pocket. In some embodiments, the firmer pad may be selected in order to apply a higher overall amount of pressure to the wound site.

In some embodiments, the predetermined amount of pressure applied by the pressure bandage when applied to the anatomical location on the body of the patient reduces or eliminates blood flow in venous capillaries of the patient. In some cases, the predetermined amount of pressure exerted by the pressure bandage when applied in the anatomical location on the body of the patient applies a pressure against the patient's blood vessels in the anatomical location of at least approximately 8 mmHG.

In some cases, the predetermined amount of pressure exerted by the pressure bandage when applied in the anatomical location on the body of the patient (i.e., on the external surface of the patient's body) may be in the range of approximately 5-30 mmHG. In some cases, the predetermined amount of external pressure may be in the range of approximately 10-25 mmHG. In some embodiments, the predetermined amount of external pressure may be in the range of approximately 15-20 mmHG. Alternatively, in some embodiments, the predetermined amount of external pressure may be in the range of approximately 5-15 mmHG.

In some embodiments, the resilient pad and the central portion of the elastic sheet may have substantially the same shape, with the central portion of the elastic sheet being larger than the resilient pad. This may ensure that the elastic sheet can adhere to the skin of the patient around the resilient pad on all sides.

Figure 6:
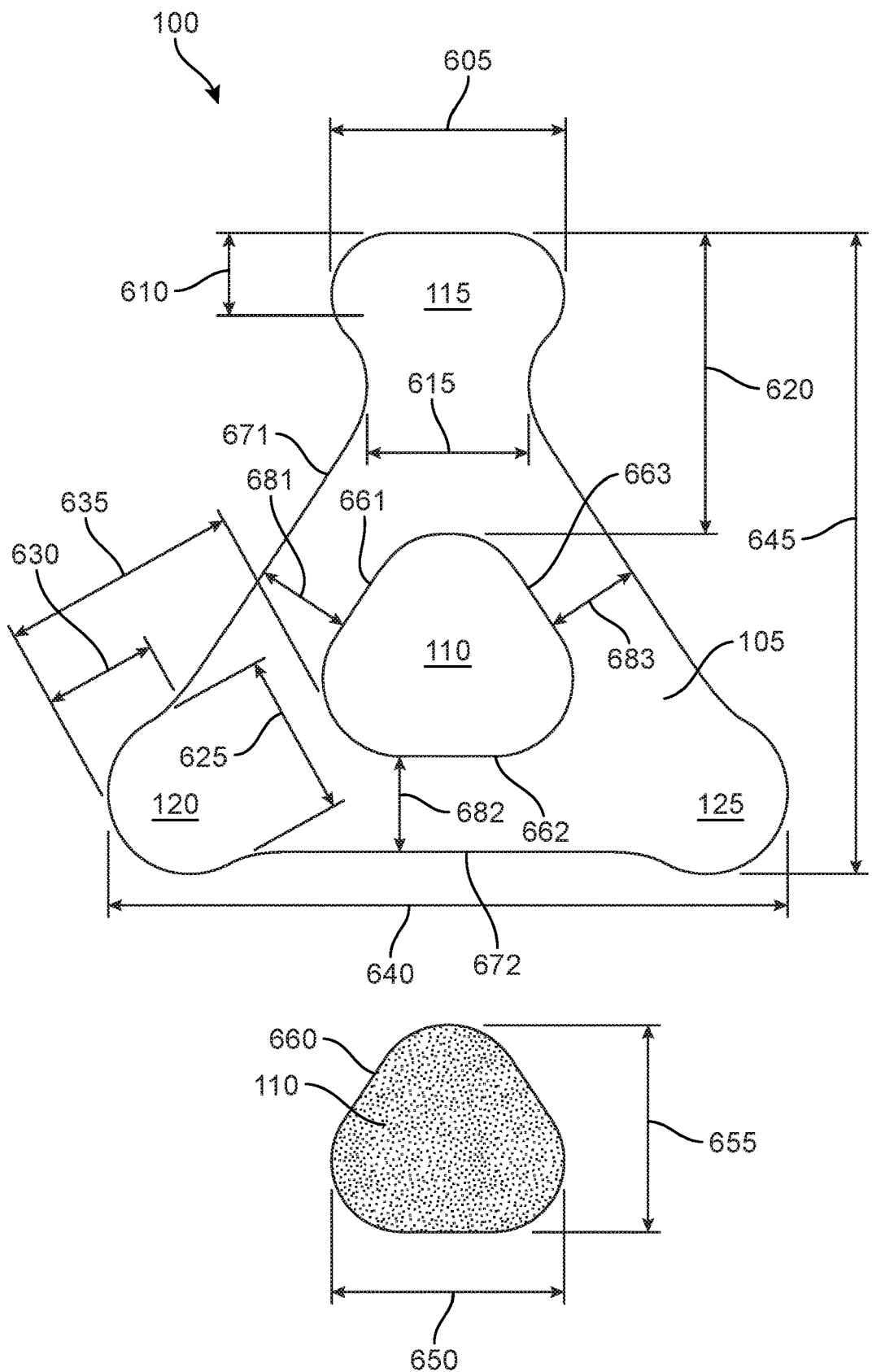
FIG. 6 is a schematic illustration of a pressure bandage according to an exemplary disclosed embodiment.

FIG. 6 is another schematic illustration of pressure bandage 100. As shown in FIG. 6, resilient pad 110 may be generally centered on elastic sheet 105. Further, in some embodiments, resilient pad 110 may have a substantially similar shape as elastic sheet 105. That is, in some embodiments, elastic sheet 105 may have a center portion with a first predetermined shape. For example, as shown in FIG. 6, in some embodiments, the center portion of elastic sheet 105 may be substantially triangular. The substantially triangular shape of the center portion of elastic sheet 105 may be formed by a first side edge 671 extending between first anchor 115 and second anchor 120, a second side edge 672 extending between second anchor 120 and third anchor 125, and a third side edge 673 extending between third anchor 125 and first anchor 115. In addition, resilient pad 110 may include peripheral edges forming a second predetermined shape. In some embodiments, the second predetermined shape may be substantially the same as the first predetermined shape of resilient pad 110 but larger. Accordingly, in some embodiments, resilient pad 110 may have a substantially triangular shape formed by a first pad edge 661, a second pad edge 662, and a third pad edge 663.

Further, in some embodiments, resilient pad 110 may be substantially centered on elastic sheet 105. That is, the peripheral edges of resilient pad 110 may be substantially equally spaced from the outer edges of the center portion of elastic sheet 105. Accordingly, first side edge 671 of elastic sheet 105 may be spaced from first pad edge 661 by a first distance 681. Second side edge 672 may be spaced from second pad edge 662 by a second distance 682. Third side edge 673 may be spaced from third pad edge 663 by a third distance 683. In some embodiments, pressure bandage 100 may have lateral symmetry. In such embodiments, first distance 681 may be substantially the same as third distance 683. In some embodiments, third distance 681 may also be substantially the same as first distance 681 and third distance 683.

Pressure bandage 100 may also include skin anchors extending radially away from resilient pad 110. For triangular configurations, such as pressure bandage 100 shown in FIG. 6, skin anchors may be formed by lobes extending from the vertices of the triangular center portion of elastic sheet 105. Accordingly, first anchor 115 is formed by a first lobe extending from a first vertex between first outer edge 671 and third outer edge 673. Second anchor 120 is formed by a second lobe extending from a second vertex between first outer edge 671 and second outer edge 672. Third anchor 125 is formed by a third lobe extending from a third vertex between the second outer edge 672 and third outer edge 673.

FIG. 6 schematically illustrates the general shape of pressure bandage 100. Elastic sheet 105 may have a sheet width 640 and a sheet length 645. Resilient pad 110 may have a pad width 650 and a pad length 655. In addition, resilient pad 110 may have a pad thickness 657 (see FIG. 8). First anchor 115 has a first width 605 and a first length 610. In addition, first anchor 115 may extend a distance 620 from peripheral edge 660 of resilient pad 110.

As shown in FIG. 6, first anchor 115 may have a relatively large width 605. This may provide a large surface area for anchoring pressure bandage 100 to the skin in the superior direction relative to the wound site. Accordingly, first anchor 115 is subjected not only to tension due to the stretching of elastic sheet 105 during application, but is also to tension resulting from the force of gravity pulling the rest of pressure bandage 100 in the inferior direction. Also, as explained in greater detail below, pressure bandage 100 may be configured to facilitate applying first anchor 115 to the skin prior to applying second anchor 120 and third anchor 125. With only first anchor 115 (and possibly a portion of the center portion of elastic sheet 105) attached to the skin, first anchor 115 may be subjected to a large amount of tension that is not necessarily experienced when all three anchors are affixed to the skin. In order to ensure that first anchor 115 remains affixed to the skin when subjected to this large tension, first anchor 115 is formed with a large surface area.

In addition, the neck region between first anchor 115 and the center portion of elastic sheet 105 may have a neck width 615. Neck width 615 may be selected to provide first anchor 115 with a tensile strength high enough to withstand the large tensile forces discussed above.

In addition, as will be discussed in greater detail below, pressure bandage 100 (or similarly shaped pressure bandages) may be applied to the upper chest region of the patient. In such embodiments, first anchor 115 may be configured to be affixed over the shoulder of the patient. In such embodiments, the width of first anchor 115 may provide a large surface area to strengthen the connection of first anchor 115 to the upper back region of the patient. In addition, in such embodiments, neck width 615 may be formed narrow enough so as to avoid undue impingement on the patient's neck in the collar region.

As shown in FIG. 6, second anchor 120 may have a second width 625 extending from the intersection of second anchor 120 with first outer edge 671 and second outer edge 672. In addition, second anchor 120 may have a second length 630 extending radially from first outer edge 671 and second outer edge 672. Further, second anchor 120 may extend a distance 635 from resilient pad 110. Although not labeled in FIG. 6, third anchor 125 may have the same or similar dimensions as second anchor 120. Thus, as shown in FIG. 6, first anchor 115 may have a first anchor shape, second anchor 120 may have a second anchor shape, and third anchor 125 may have a third anchor shape. As further shown in FIG. 6, second anchor 120 and third anchor 125 may have the same or substantially similar shape. As also shown in FIG. 6, first anchor 115 may have a substantially different shape than second anchor 120 and third anchor 125.

It will be noted that the lateral symmetry of pressure bandage 100 shown in FIG. 6 may enable pressure bandage 100 to be applied to either side of the body. In some embodiments, the pressure bandage may have a laterally asymmetric configuration in order to optimize application to one side of the body or the other.

In some embodiments, the liner or liner applied to the adhesive side of the elastic sheet may be configured to facilitate application of the pressure bandage. For example, in some embodiments, the liner may include indicia indicating the orientation at which the pressure bandage should be applied. Additionally, in some embodiments, the liner may include a plurality of cut lines configured to facilitate removal of sections of the liner in a particular order that provides application of the pressure bandage in the most consistent and effective way. In some embodiments, the cut lines may be configured with curves that facilitate peeling the sections separated by the cut lines. Further, the liner may include indicia, such as numbers, indicating the order in which the sections of liner should be removed, and thus the order in which the areas of the pressure bandage should be applied to the body of the patient.

Figure 7:
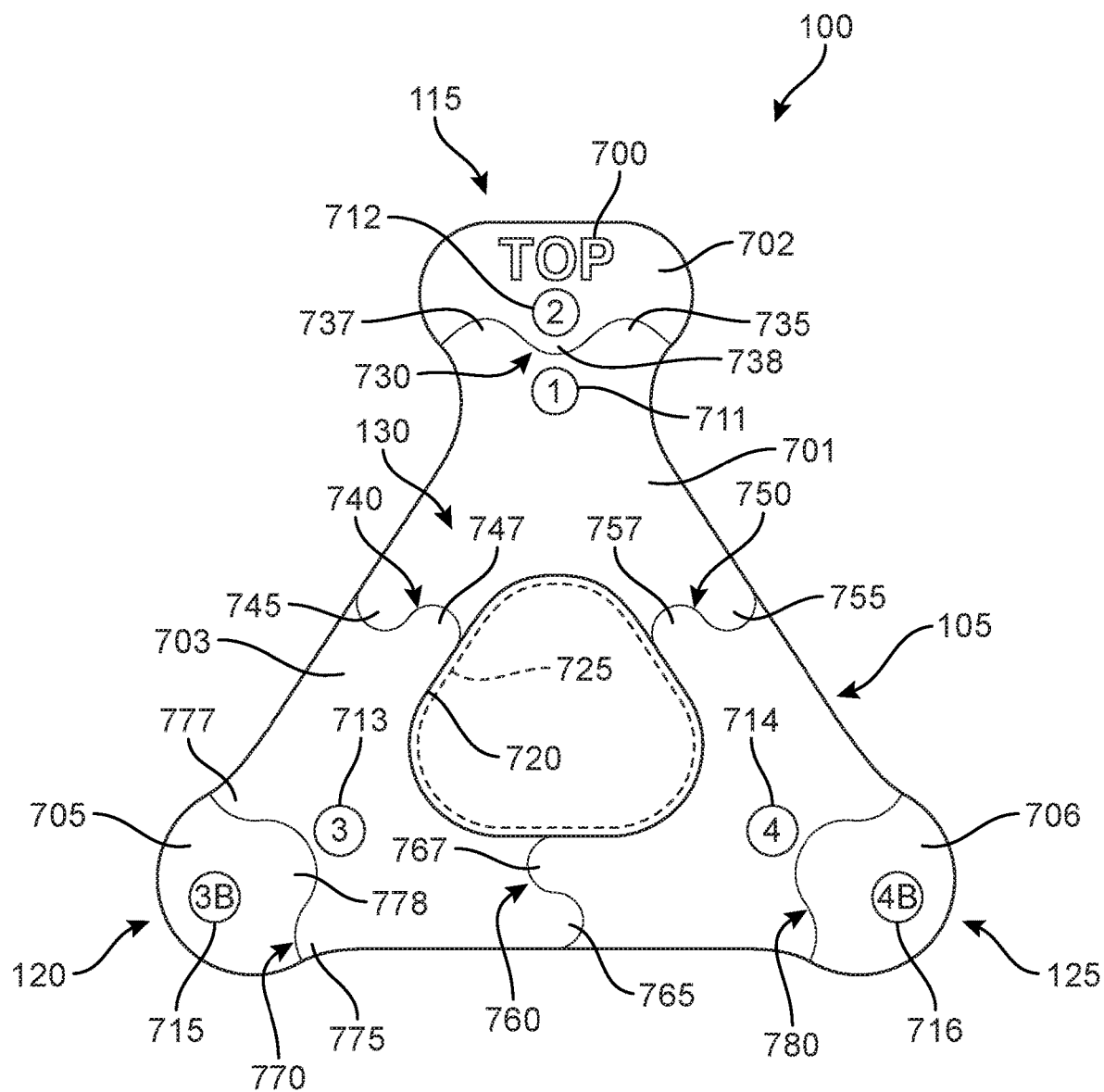
FIG. 7 is a schematic illustration of the pressure bandage of FIG. 6 showing cut lines of the liner.

FIG. 7 is a schematic illustration of pressure bandage 100 showing liner 130 affixed to the adhesive side of the elastic sheet. As shown in FIG. 7, liner 130 may include indicia, such as an orientation label 700. As shown in FIG. 7, orientation label 700 may indicate which side of pressure bandage 100 should be oriented in the superior direction on the patient. In bandages configured to be applied to other anatomical regions of the body, different orientation labels may be used.

As also shown in FIG. 7, liner 130 may include a plurality of cut lines separating liner 130 into distinct sections. For example, as shown in FIG. 7, liner 130 may be separated into a first section 701, a second section 702, a third section 703, a fourth section 704, a fifth section 705, and a sixth section 706. First section 701 may include a first indicia 711, second section 702 may include a second indicia 712, third section 703 may include a third indicia 713, fourth section 704 may include a fourth indicia 714, fifth section 705 may include a fifth indicia 715, and sixth section 706 may include a sixth indicia 716. First indicia 711, second indicia 712, third indicia 713, fourth indicia 714, fifth indicia 715, and sixth indicia 716 may indicate a suggested order in which the sections of liner 130 should be removed.

Further, the cut lines may be configured to facilitate removing the distinct sections of liner 130 in a predetermined sequence. For example, for applying a bandage having the shape of pressure bandage 100 to a front portion of the patient's torso, the upper portions of the bandage may be affixed to the skin first. A first section 701 of liner 130 should be removed first and the adhesive area of the elastic sheet covered by first section 701 should be affixed to the skin first. Accordingly, first indicia 711 (shown, for example, in FIG. 7 as a circled "1") may indicate that first section 701 should be removed first. By applying the portion of the bandage corresponding with first section 701 of liner 130 to the skin first, at least a portion of the bandage is held against and applied to the wound site before pulling any anchors of the bandage, thus ensuring that the resilient pad is positioned as desired over the wound site.

It will be noted that, while the resilient pad is not shown in FIG. 7, a dashed line 725 indicates the location of the peripheral edge of the pad. The inner edge 720 of liner 130 is shown in FIG. 7 to be slightly spaced from dashed line 725. This slight spacing between inner edge 720 of liner 130 and the peripheral edge of the resilient pad may facilitate the removal of sections of liner 130 without binding against the peripheral edge of the resilient pad. In other embodiments, there may be substantially no spacing between inner edge 720 of liner 130 and the peripheral edge of the resilient pad.

With the resilient pad held (by hand) against the wound site and the first section 701 of elastic sheet 105 held against the skin proximate the wound site, first anchor 115 may be pulled radially away from the resilient pad and then affixed to the skin. While positioning the bandage to affix the section of elastic sheet 105 corresponding with first section 701 to the skin, a second section 702 of liner 130 may be left attached to elastic sheet 105. This may facilitate handling anchor 115 while orienting the bandage. Once the bandage is oriented and the portion of elastic sheet 105 corresponding with first section 701 is affixed to the skin, second section 702 may be removed from first anchor 115, then first anchor 115 may be pulled firmly, and first anchor 115 may be affixed to the skin. A second indicia 712 may indicate that second section 702 should be the next section of liner 130 removed.

In some embodiments, the cut lines between sections of liner may have shapes that facilitate peeling the sections of liner in the desired order. For example, in some embodiments, the cut lines may have curves that form interlocking convex and concave portions. The convex portions form tabs under which the user can place a finger or thumb in order to begin peeling the section of liner off the elastic sheet. In some embodiments, the convex portions may be oriented in a direction that facilitates peeling when the bandage is in a predetermined condition during the bandage application process. That is, during the bandage application process, some portions of the bandage are adhered to the skin and other portions of the bandage are not. In order to facilitate peeling of a given section of liner when the bandage is partially affixed to the skin, a convex portion of the next section of liner to be peeled may be oriented in a direction that makes the convex portion of liner accessible when the bandage is partially affixed to the skin.

First section 701 and second section 702 of liner 130 may be separated by a first cut line 730. First cut line 730 may have a curved configuration defining interlocking convex and concave portions of liner 130. For example, first section 701 of liner 130 may include a first convex portion 735 and a second convex portion 737 defined by first cut line 730. First convex portion 735 and second convex portion 737 may interlock with corresponding concave portions of second section 702 of liner 130. In addition, first cut line 730 may also define a third convex portion 738 of second section 702 of liner 130. The first place to peel first section 701 may be first convex portion 735 (or second convex portion 737), which is located adjacent the peripheral edge of elastic sheet 105. In addition, a second cut line 740 may define a fourth convex portion 745 in first section 701 of liner 130 and a fifth convex portion 750 in third section 703 of liner 130. Thus, the inferior portion of first section 701 may be peeled beginning with fourth convex portion 745, which is located adjacent the peripheral edge of elastic sheet 105. Similarly, on the other side of pressure bandage 100, a third cut line 750 may define a sixth convex portion 755 of first section 701 of liner 130 and a seventh convex portion 757 in fourth section 704 of liner 130.

Once first section 701 of liner 130 is removed, and the section of elastic sheet 105 is affixed to the skin as discussed above, second section 702 of liner 130 may be peeled from first anchor 115, beginning with third convex portion 738. Then first anchor 115 may be pulled firmly in a radial direction away from the resilient pad and affixed to the skin.

At this point during the application process, first section 701 and second section 702 are affixed to the skin of the patient. Next, third section 703 may be removed to begin the process of affixing second anchor 120 to the skin. It will be noted that the order in which second anchor 120 and third anchor 125 are applied may be reversed for different applications. Generally, for off-center applications of pressure bandage 100, application of the bandage can be facilitated and effective if the anchor that will wrap around the side of the patient is applied prior to the anchor that extends across the midline of the patient's torso.

There are at least two reasons that this order of application may be beneficial. First, postoperative patients are typically lying on their backs. This limits how far the anchor can be wrapped around the patient's side. If the midline anchor is affixed first, and then the side anchor is pulled around the side of the patient, the hospital bed may prevent the side anchor from being pulled far enough for the resilient pad to apply the magnitude of pressure that is desired. Accordingly, to ensure that the desired pressure is applied by the bandage, the side anchor may be affixed to the patient before the midline anchor. That is, the side anchor can be pulled as far around the patient as desired, or as limited by the hospital bed. Then, the midline anchor may be pulled across the patient's torso. The second reason for applying the side anchor first is that, once the side anchor is affixed to the skin, the wrapping of the side anchor around the side of the patient provides a secure attachment against which the midline anchor may be pulled across the torso. Accordingly, since the side anchor is to be applied first, the description of FIG. 7 is for applying pressure bandage 100 off-center to the left side of the body.

As shown in FIG. 7, third section 703 may include third indicia 713 indicating the step at which third section 703 of liner 130 should be removed. Third section 703 of liner 130 is defined by second cut line 740, fourth cut line 760, and fifth cut line 770. Fourth cut line 760 may define an eighth convex portion 765 in third section 703 and a ninth convex portion 767 in fourth section 704 of liner 130. Fifth cut line 770 may define a tenth convex portion 775 and an eleventh convex portion 777 in third section 703. In addition, fifth cut line 770 may define a twelfth convex portion 778 in fifth section 705 of liner 130. In order to peel third section 703 of liner 130, one or more of fifth convex portion 747, eighth convex portion 765, tenth convex portion 775, and eleventh convex portion 777 may be pulled. Each of eighth convex portion 765, tenth convex portion 775, and eleventh convex portion 777 are located adjacent the peripheral edge of elastic sheet 105, which may facilitate placing a finger or thumb underneath these portions.

In some embodiments, the configuration of fourth cut line 760 may be reversed. By reversing cut line 760, the orientation of eighth convex portion 765 may also be reversed. This would facilitate removal of fourth section 704 of liner 130 prior to third section 703. This, in turn, would facilitate application of fourth section 704 to the body prior to third section 703, which, as discussed above, may be suitable for application of the pressure bandage off-center to the right of the patient's torso, instead of off-center to the left.

Once third section 703 of liner 130 has been removed, the area of elastic sheet 105 from which third section 703 was removed may be affixed to the skin of the patient. With the areas of elastic sheet 105 corresponding with first section 701, second section 702, and third section 703 of liner 130.

At this point, a choice may be made as to the order in which the remaining sections of liner 130 are removed. The order may be chosen based on the patient's anatomy, the type of implantable device over which the bandage is being applied, the location on the body that the bandage is applied, or the user's personal preference. Choices for the final sequence of liner removal include the following. In one possible sequence, fourth section 704 may be removed, then fifth section 705, followed by sixth section 706. This sequence ensures secure fixation proximate the resilient pad prior to application of second anchor 120 and third anchor 125. Another possible sequence may be to remove fourth section 704, sixth section 706, and then fifth section 705. In some case, this alternative may be efficient because the user can work with sixth section 706 immediately after fourth section 704 to which sixth section 706 is adjacent. That is, the user will already be working with that corner of the bandage (i.e., in fourth section 704), so staying in that corner (i.e., with sixth section 706) enables the user to quickly transition. As another possible sequence, after removing third section 703 and affixing the corresponding portion of elastic sheet 105 to the body, the user may then remove fifth section 705, then fourth section 704, followed by sixth section 706. This may facilitate attachment of second anchor 120 completely before moving to third anchor 125. As discussed above, attaching the side anchor, which is second anchor 120 in this case, has at least two particular benefits. It will be understood that the order in which sections of the liner are removed may vary. Further, in some cases, more than one section of liner may be removed at a time. In addition, the configuration of cut lines may vary depending on the size and shape of the bandage and/or depending on the anatomical location in which the bandage is to be used.

Figure 8:
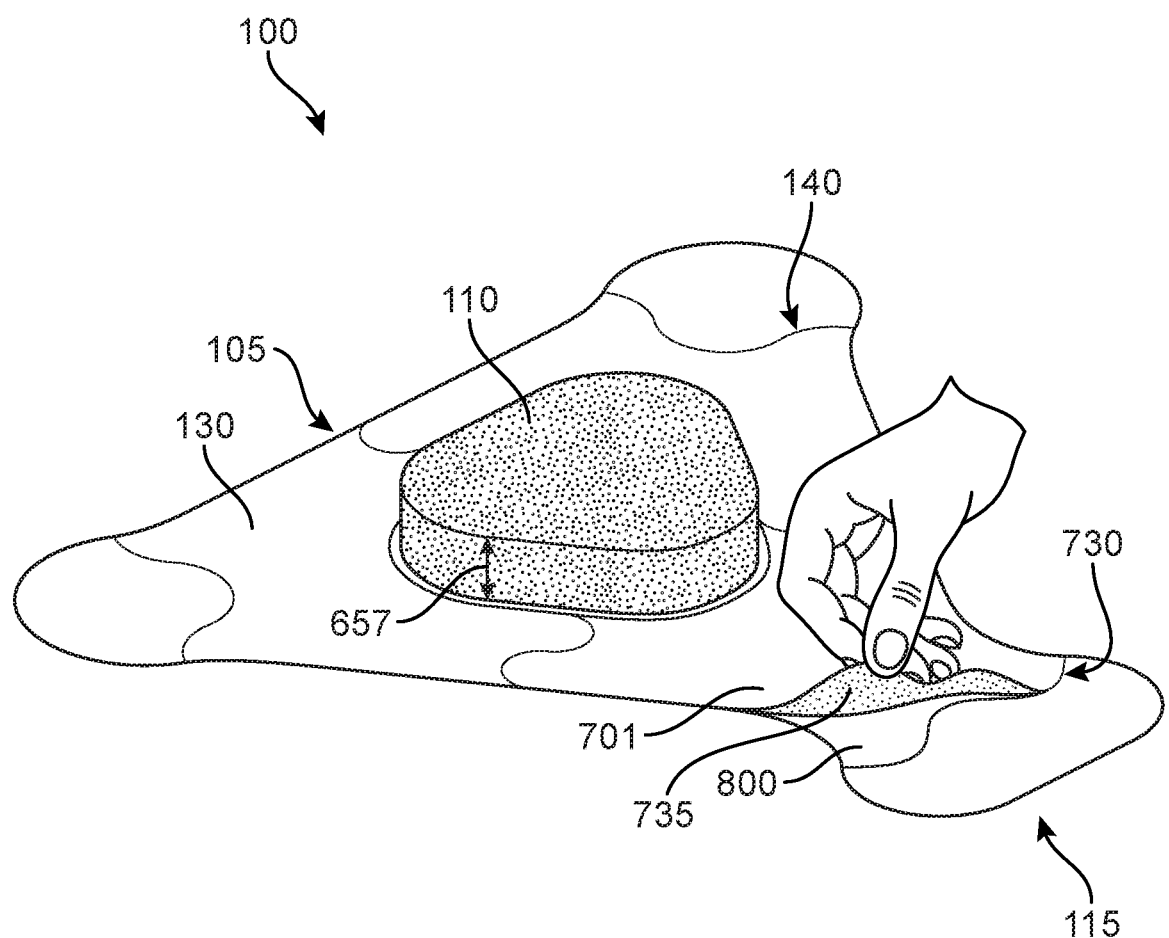
FIG. 8 is a schematic illustration of a section of the liner being peeled off of the elastic sheet.

FIG. 8 is a schematic illustration of liner 130 being peeled from elastic sheet 105. As shown in FIG. 8, first concave portion 735 of first section 701 of liner 130 is being peeled away from adhesive surface 800 of elastic sheet 105.

Resilient pad 110 may be sized and shaped to provide pressure to a surgical pocket for differently shaped implantable devices. Resilient pad 110 need not necessarily have the same shape as the medical device over which it is applied. However, in some embodiments, it may be beneficial if the skin contacting surface area of resilient pad 110 is large enough to fully cover the medical device regardless of whether the resilient pad and the medical device have the same shape.

In some embodiments, a system may be provided including an implantable medical device configured to be implanted at an anatomical location proximate the surface of the skin; and a pressure bandage configured to be applied to a surgical site from the implantation of the medical device. For example, in some cases, the medical device may be configured to be implanted subcutaneously. In other cases, the medical device may be configured to be implanted submuscularly. In still other cases, the medical device may be configured to be implanted under other tissues located proximate to the skin. The pressure bandage may include an elastic sheet having a first predetermined shape that is configured to be applied to the anatomical location at which the medical device is configured to be implanted. In addition, the implantable medical device may have a size that corresponds with a size of the resilient pad.

Figure 9:
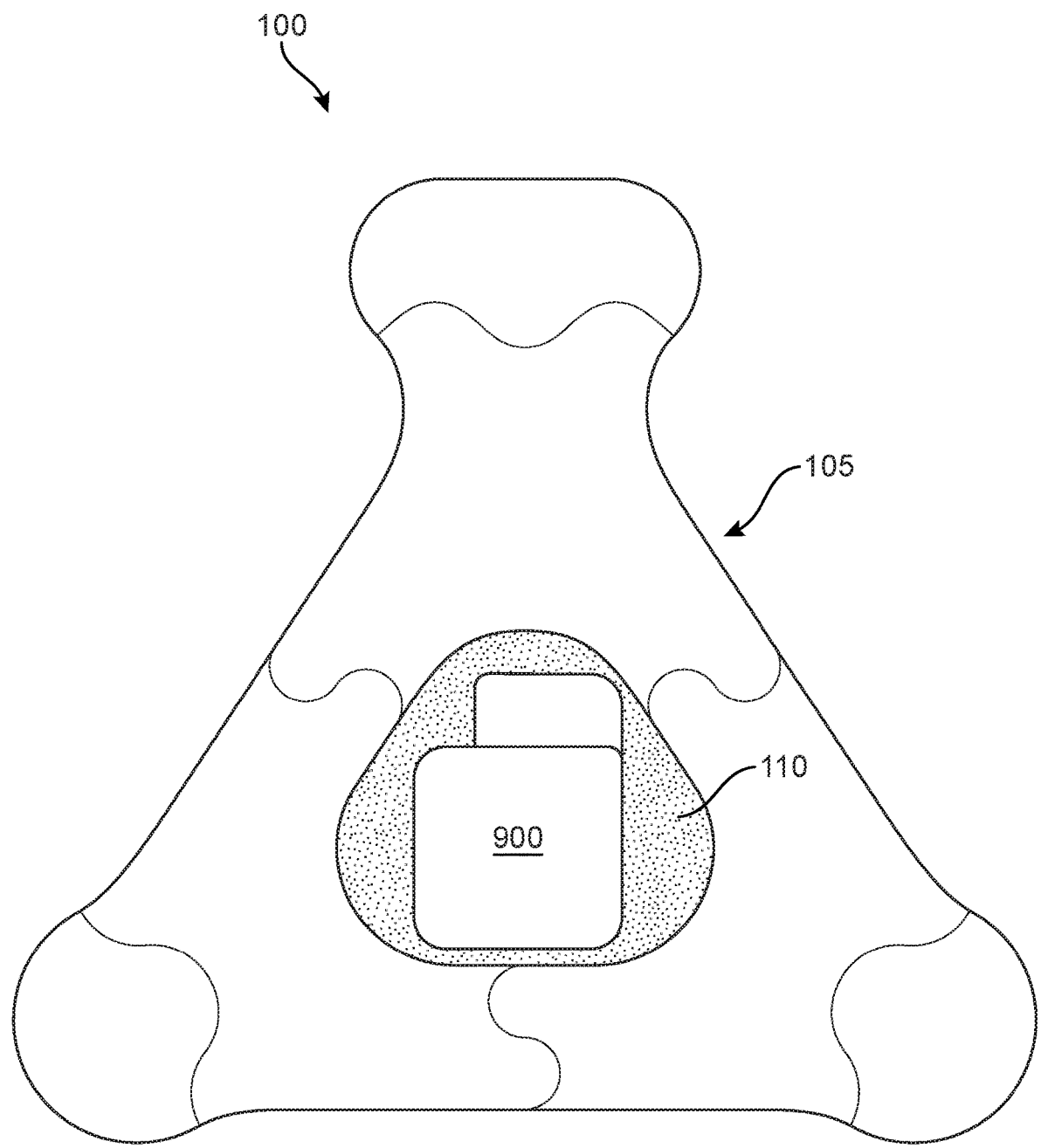
FIG. 9 is a schematic illustration showing the relative size of a pad of a pressure bandage compared to the size of an exemplary implantable medical device over which the pressure bandage may be applied.

FIG. 9 is a schematic illustration showing the relative size and shape of resilient pad 110 of pressure bandage 100 compared to the size and shape of an exemplary implantable medical device 900 over which pressure bandage 100 may be applied. Medical device 900, as shown in FIG. 9, has a hypothetical shape that is based loosely on the shapes of certain commercially available implantable devices over which pressure bandage 100 may be applied. Medical device 900 is intended to schematically illustrate an irregular shape relative to the substantially triangular shape of resilient pad 110. As shown in FIG. 9, the outer periphery of medical device 900 may fall completely within the outer boundary of resilient pad 110.

Figure 10:
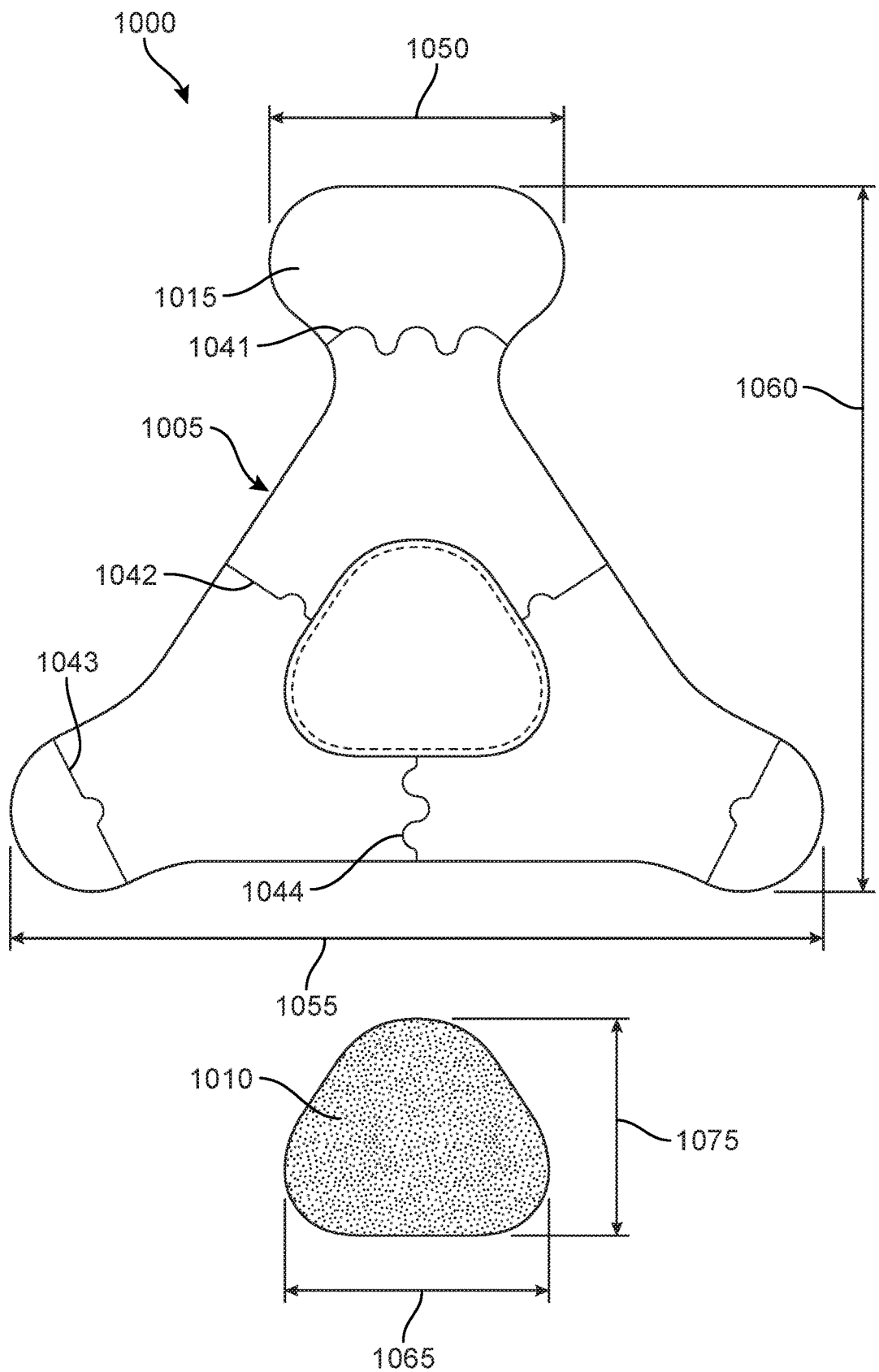
FIG. 10 is a schematic illustration of a pressure bandage according to another exemplary disclosed embodiment.

FIG. 10 is a schematic illustration of a pressure bandage according to another exemplary disclosed embodiment. As shown in FIG. 10, a pressure bandage 1000 may include an elastic sheet 1005 and a resilient pad 1010. The materials and general configurations of elastic sheet 1005 and resilient pad 1010 may be substantially similar to the embodiment shown in FIGS. 1-9. Particular differences in the embodiment shown in FIG. 10 include the precise shapes of elastic sheet 1005 and resilient pad 1010. Elastic sheet 1005 may have a first width 1055 and a first length 1060. First width 1055 and first length 1060 may be substantially similar to the dimensions of elastic sheet 105. However, a first anchor 1015 may have an anchor width 1050 that is substantially wider than first anchor 115 of elastic sheet 105. This wider anchor may facilitate application of pressure bandage 1000 to different portions of the body that may require stronger fixation at the first anchor.

In addition, resilient pad 1010 may have a second width 1065 and a second length 1075. While second width 1065 may be substantially similar to that of resilient pad 110, second length 1075 may be at least slightly shorter than that of resilient pad 110. The shorter length of resilient pad 1010 may lengthen the amount of adhesive surface area between resilient pad 1010 and the distal tip of first anchor 1015.

Also, as shown in FIG. 10, the liner may have differently configured cut lines. For example, a first cut line 1041 has additional curves defining more convex portions to the adjacent sections of the liner. A second cut line 1042 and a third cut line 1043 may each have a curved portion and one or more straight portions. This may facilitate removal of the liner sections in varying order. For example, a cut line having a straight segment adjacent to the outer edge of the liner, wherein the segment is perpendicular to the edge of the liner, may facilitate peeling either of the adjacent liner sections before the other. In addition, a fourth cut line 1044 may have both additional convex portions and straight segments. This may increase the flexibility to remove the liner sections in varying ways and sequences.

Pressure bandages having significantly different shapes may also implement similar principles to those discussed above. For example, in some embodiments, the elastic sheet and/or the resilient pad may be substantially circular. In addition, a widened anchor may be used for anatomical locations other than the superior portion of the bandage, and possibly in more than one location on the same bandage.

Figure 11:
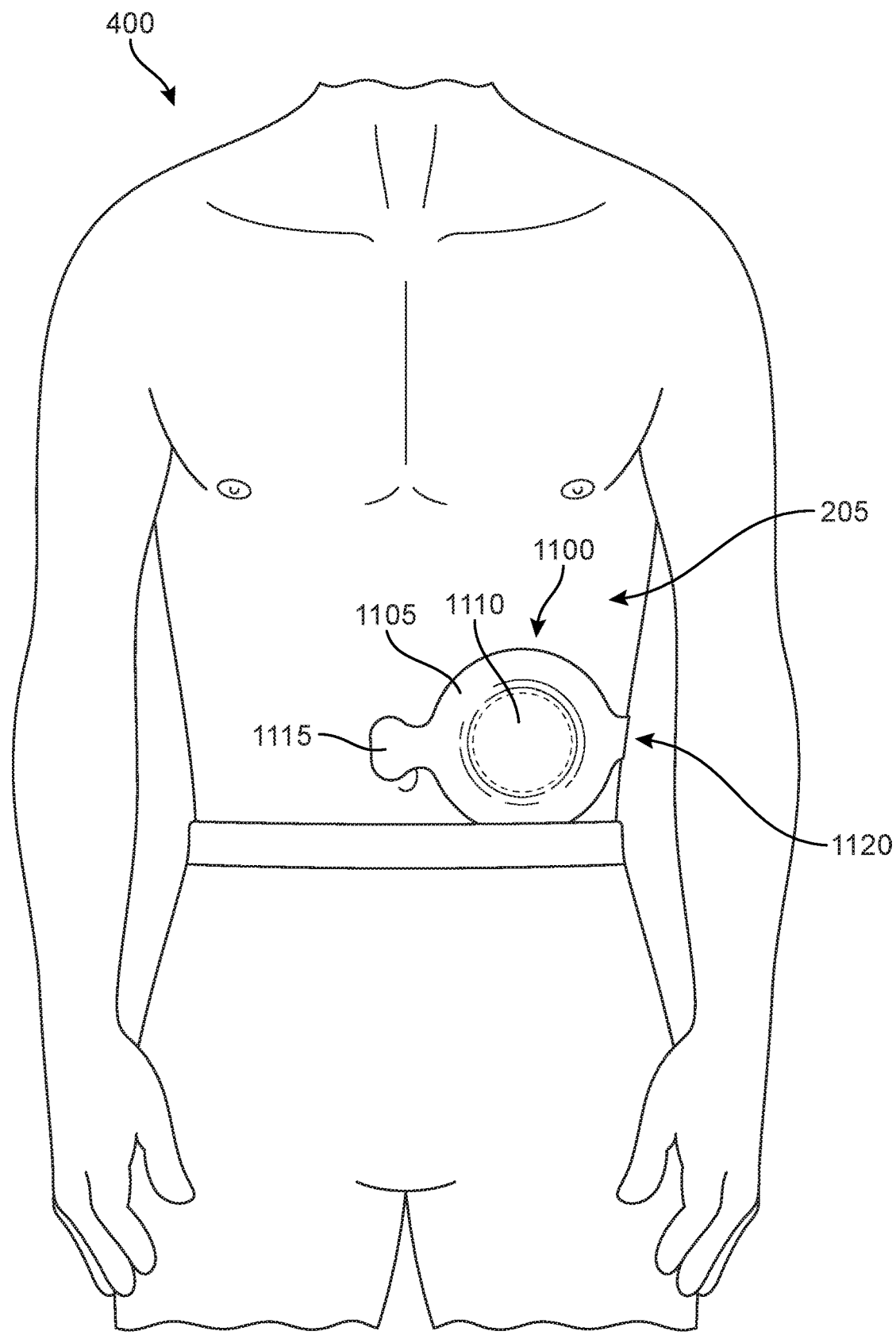
FIG. 11 is a schematic illustration of the patient shown in FIG. 4 with another exemplary pressure bandage applied to the surgical site.

FIG. 11 is a schematic illustration of the patient shown in FIG. 4 with another exemplary pressure bandage applied to the surgical site. As shown in FIG. 11, a pressure bandage 1100 may be applied to abdominal region 205 of patient 400. As further shown in FIG. 11, pressure bandage 1100 may include an elastic sheet 1105 and a resilient pad 1110. Both elastic sheet 1105 and resilient pad 1110 may have substantially circular shapes. In addition, elastic sheet 1105 may include a first anchor 1115 and a second anchor 1120 (shown wrapped around the side of the patient). As shown in FIG. 11, first anchor 1115 may have a widened shape. Although not shown in FIG. 11, second anchor 1120 may also have the same or similar widened shape. With only two anchors, the additional surface area of widened anchors may provide improved fixation adhesion to compensate for having one fewer anchor.

Pressure bandages with the same or similar configurations may be applied to different portions of the body. For example, pressure bandages configured for application in the lower abdominal region may be similarly applied to the lower lumbar region.

Figure 12:
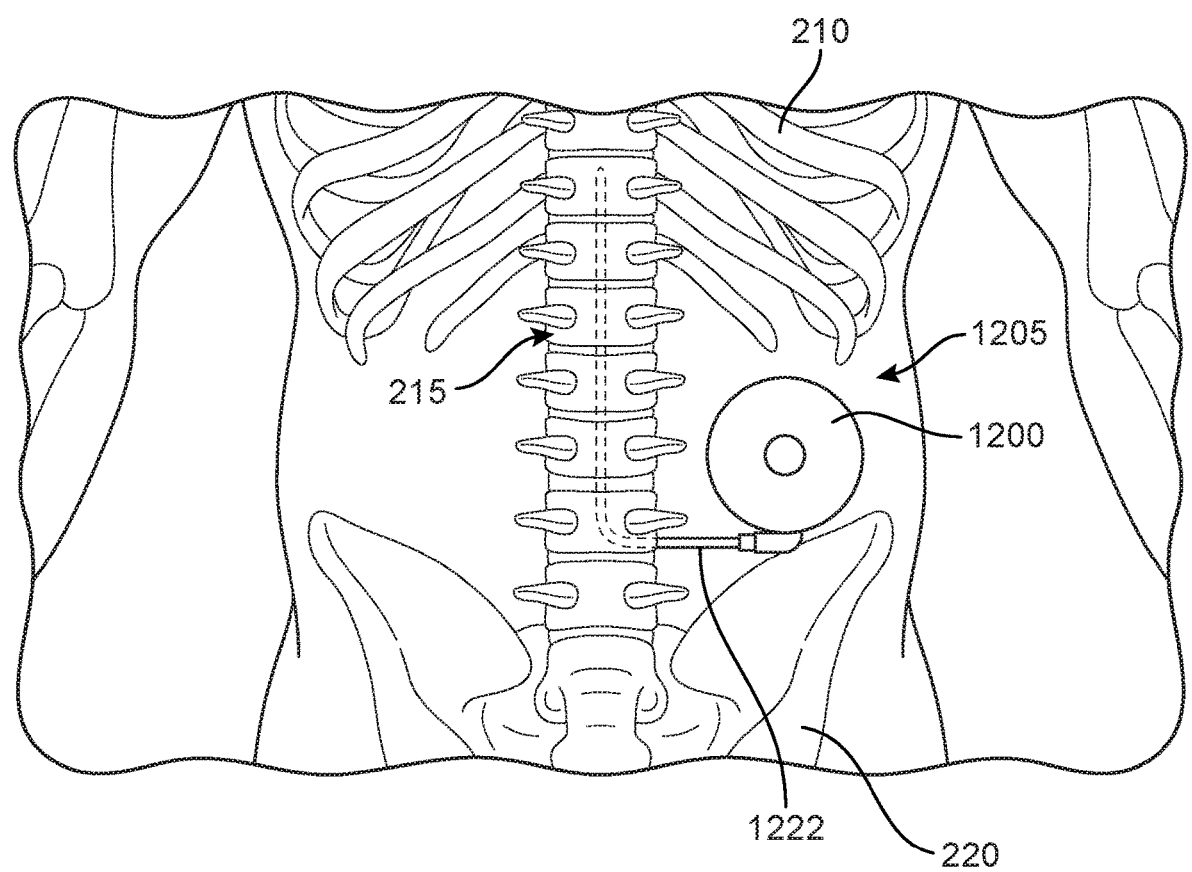
FIG. 12 is a schematic illustration of a patient with an implantable medical device located in the lumber back region.

FIG. 12 is a schematic illustration of a patient with an implantable medical device located in the lumbar back region. As shown in FIG. 12, a lumbar medical implant 1200 implanted in the lower lumbar region 1205. Implant 1200 may include a lead 1222, which may deliver either fluid and/or may include electrical leads for administering electrotherapy.

Figure 13:
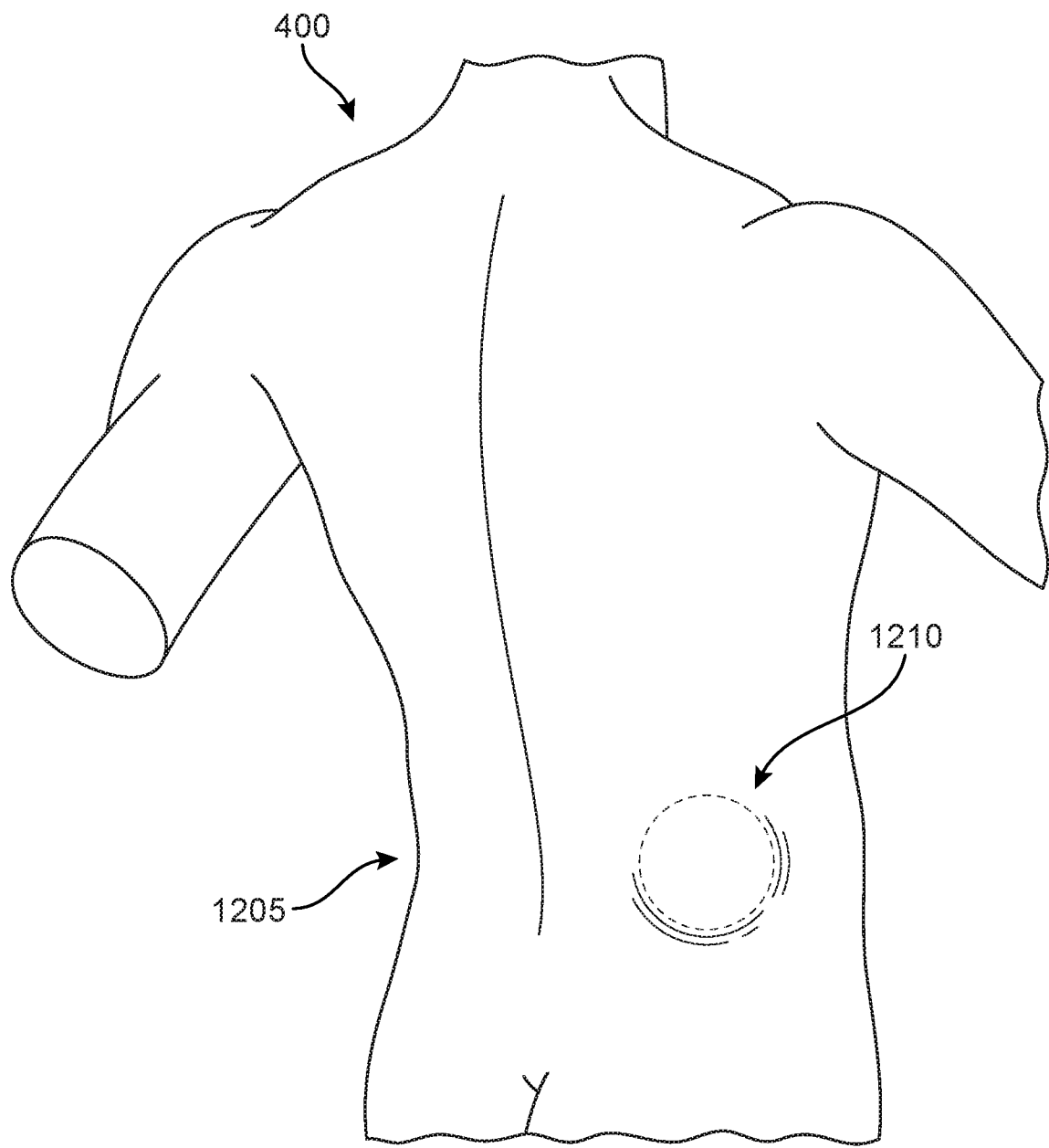
FIG. 13 is a schematic illustration of a patient with a bulge associated with a lumbar implant surgical site.

FIG. 13 is a schematic illustration of patient 400 with a bulge 1210 associated with the lumbar implant surgical site in which implant 1200 may be implanted. It will be noted that implant 1200 may be inserted on either side of lower lumbar region 1205.

Figure 14:
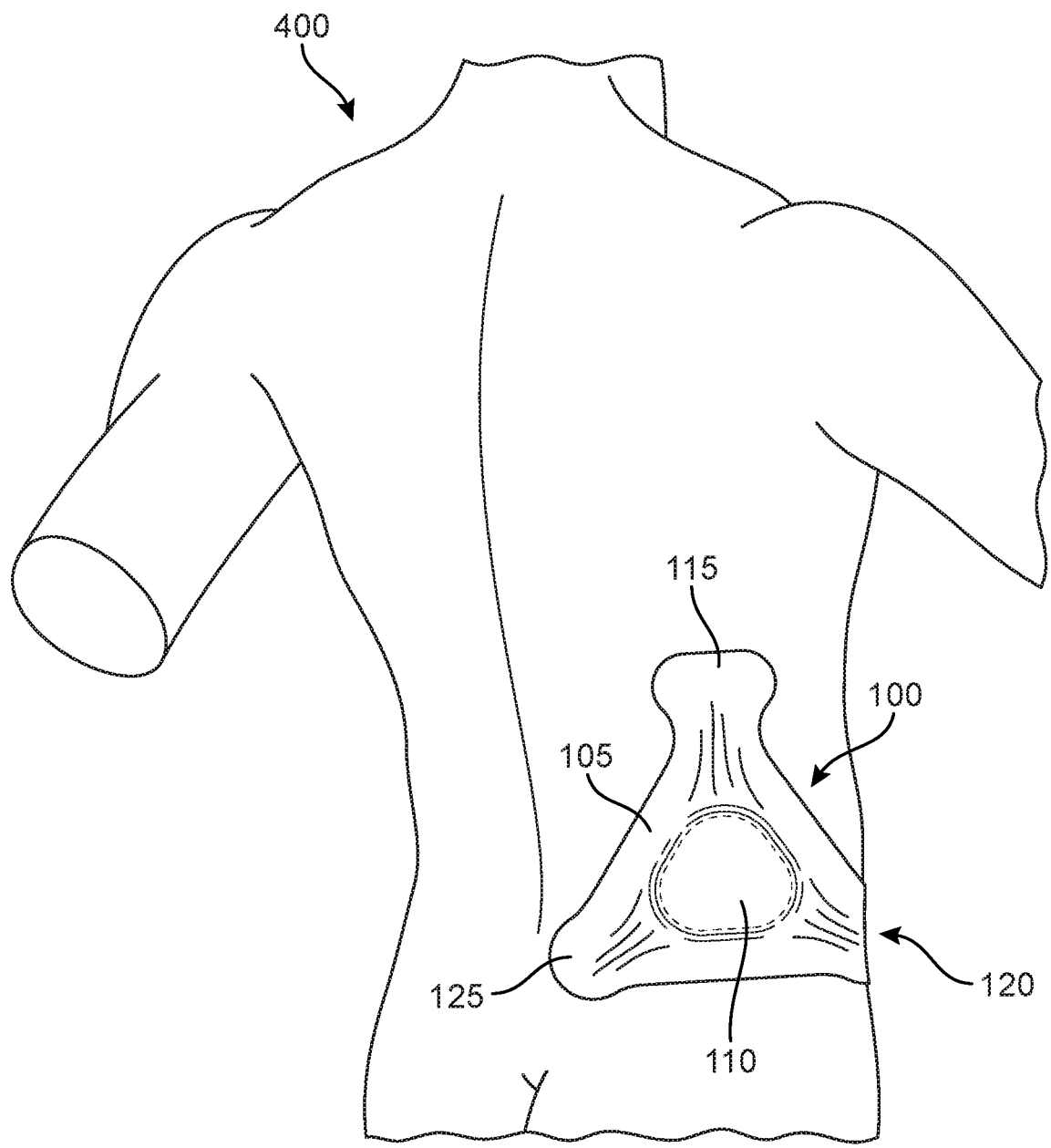
FIG. 14 is a schematic illustration of the patient shown in FIG. 13 with an exemplary pressure bandage applied to the lumbar surgical site.

FIG. 14 is a schematic illustration of patient 400 with pressure bandage 100 applied to the lumbar surgical site. As shown in FIG. 14, pressure bandage 100 may be applied to the lower lumbar region in a similar way as it is applied to the lower abdominal region. In particular, first anchor 115 is located in a superior position, second anchor 120 may be wrapped around the side of the patient, and third anchor 120 may extend laterally across the midline of the patent's torso.

Figure 15:
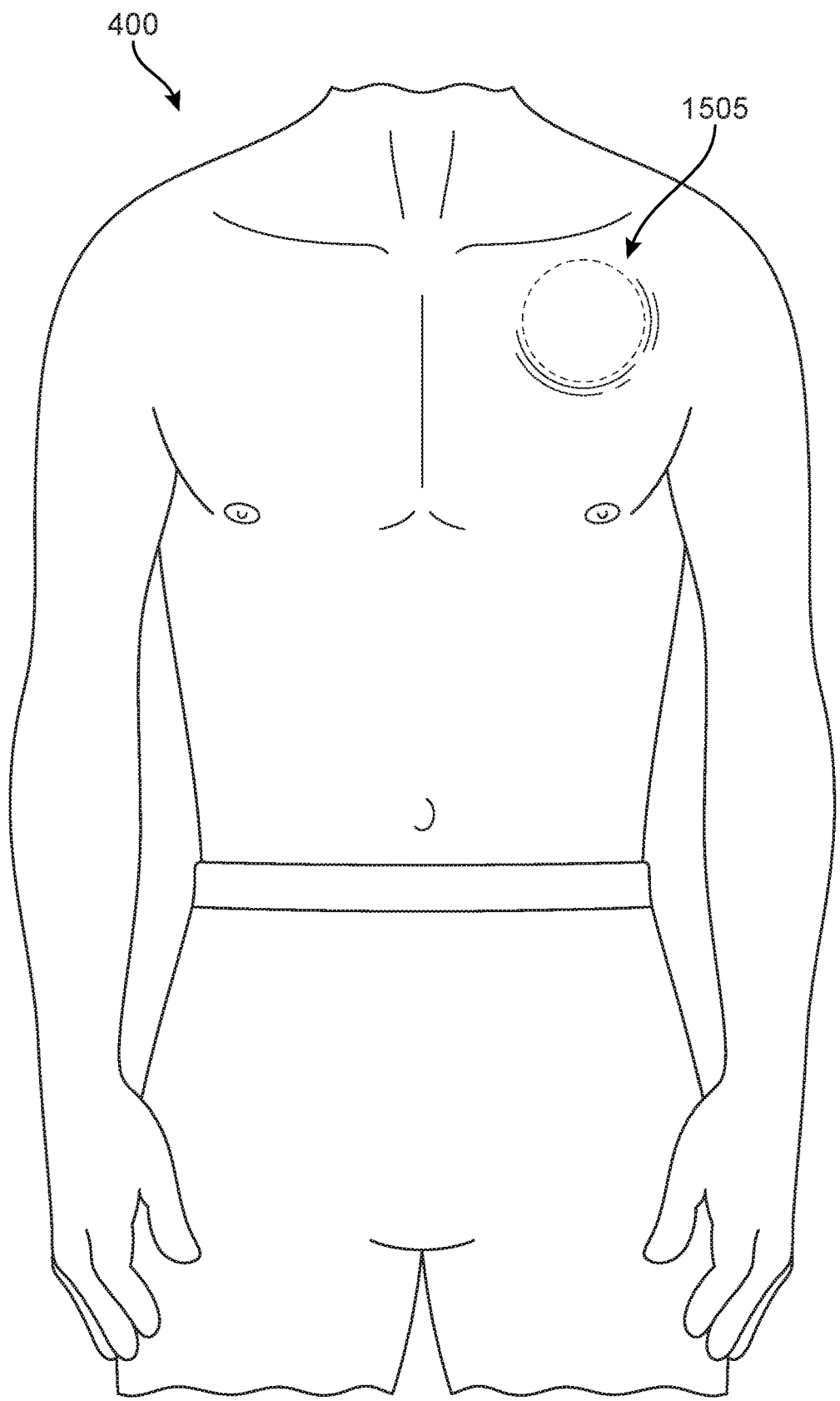
FIG. 15 is a schematic illustration of a patient with a bulge associated with an upper chest implant surgical site.

FIG. 15 is a schematic illustration of patient 400 with a bulge 1505 associated with an upper chest implant surgical site. Exemplary implantable medical devices that may be implanted in the upper chest region include pacemakers, defibrillators, medication injection ports, and other various implantable devices.

Figure 16:
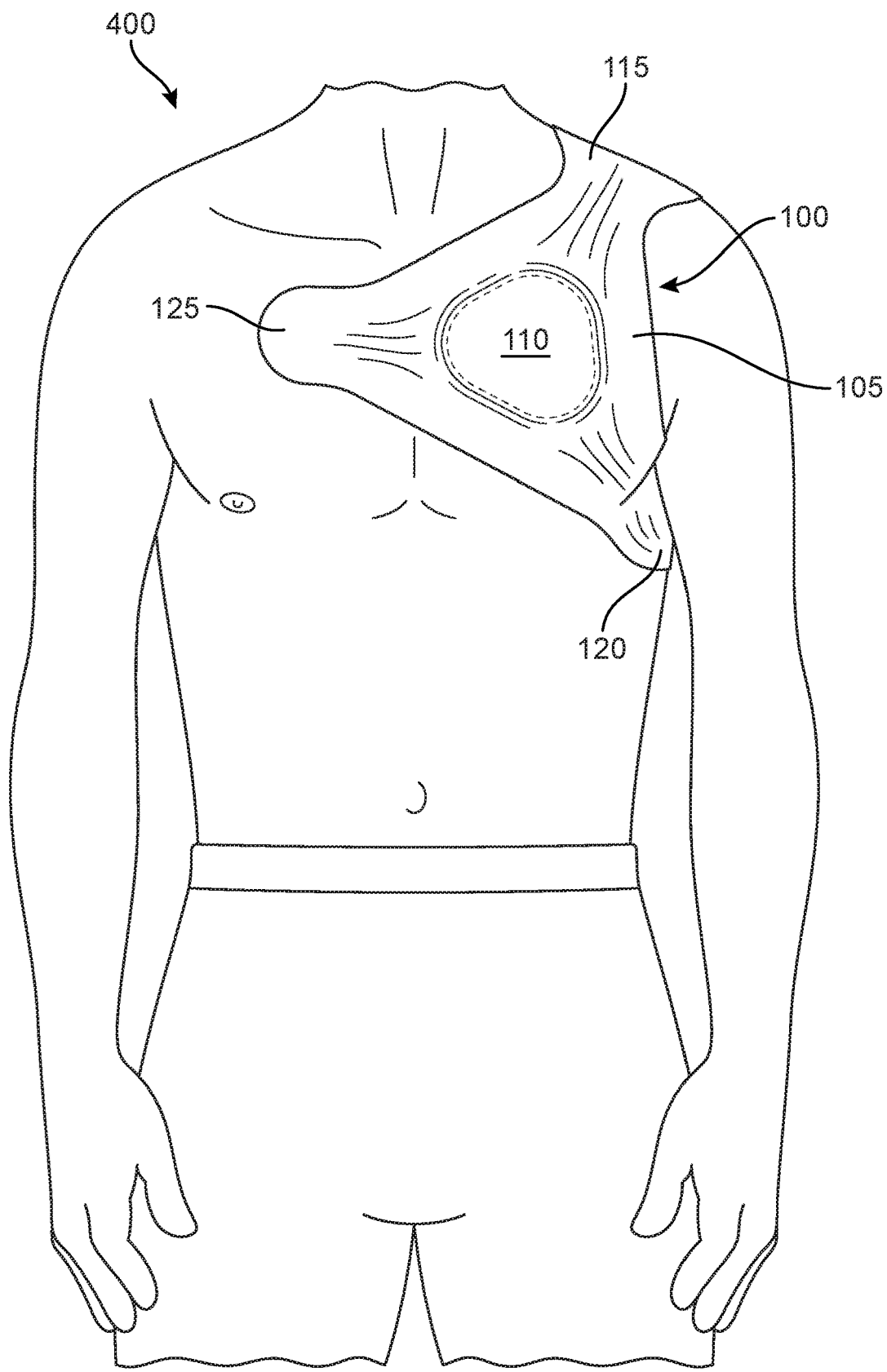
FIG. 16 is a schematic illustration of the patient shown in FIG. 15 with an exemplary pressure bandage applied to the upper chest surgical site.
Figure 17:
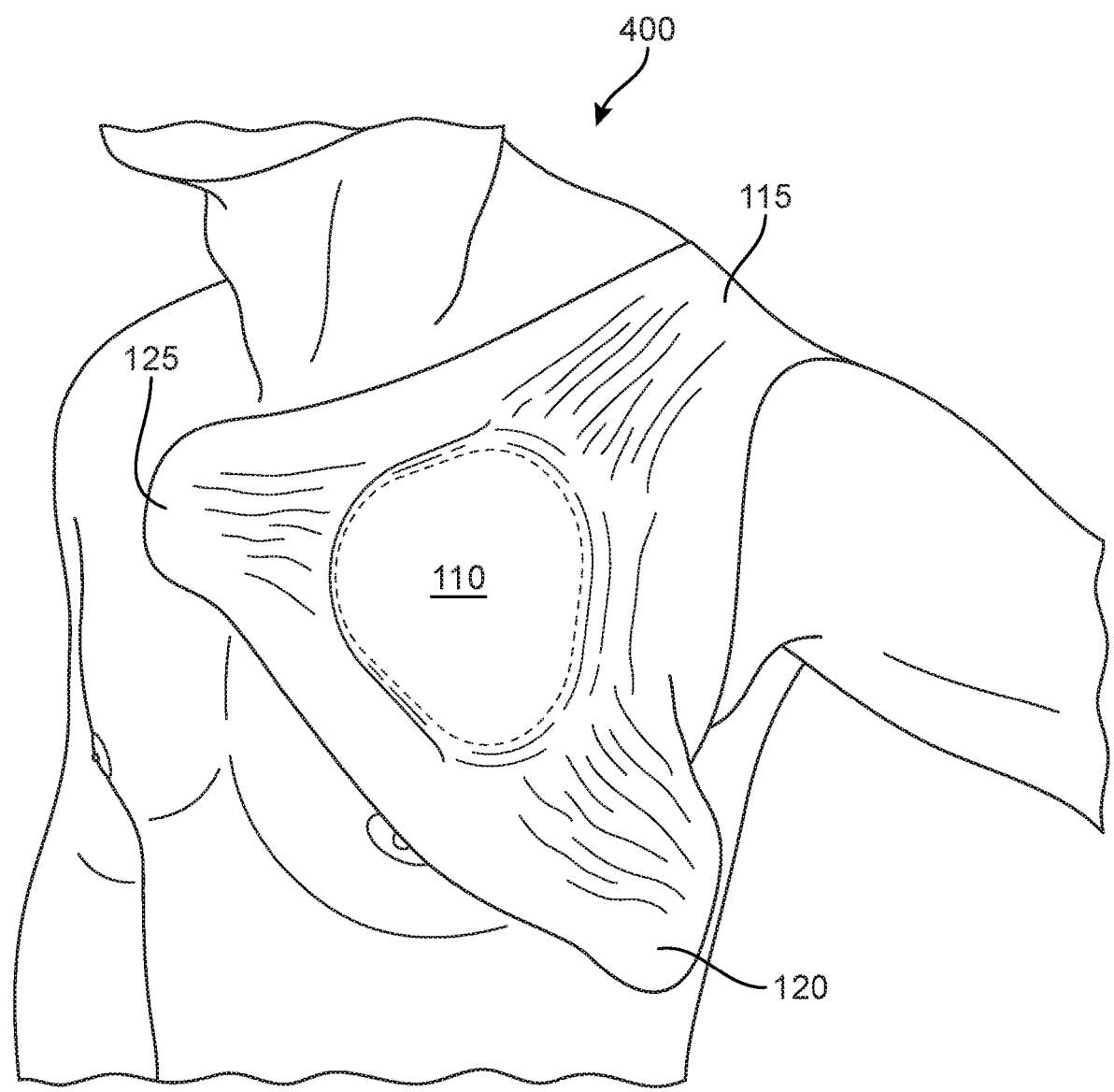
FIG. 17 is a schematic illustration of an anterior-lateral perspective view of a pressure bandage applied to the upper chest surgical site.

FIG. 16 and FIG. 17 are schematic illustrations of patient 400 with pressure bandage 100 applied to the upper chest surgical site shown in FIG. 15. As shown in FIGS. 16 and 17, first anchor 115 of pressure bandage 100 may be applied over the patient's shoulder. Second anchor 120 may be wrapped around the side of the patient, under the patient's arm. Third anchor 125 may extend across the midline of the patient's torso. Accordingly, the process of applying pressure bandage 100 to the upper chest region may be substantially similar to the process of applying pressure bandage 100 to the lower abdominal region discussed above.

The application of pressure bandages such as those discussed above may enable a predictable amount of pressure to be applied by the bandage, and the bandage may be applied much more quickly than makeshift pressure dressings formed of multiple pieces of gauze padding and several strips of medical tape.

Figure 18:
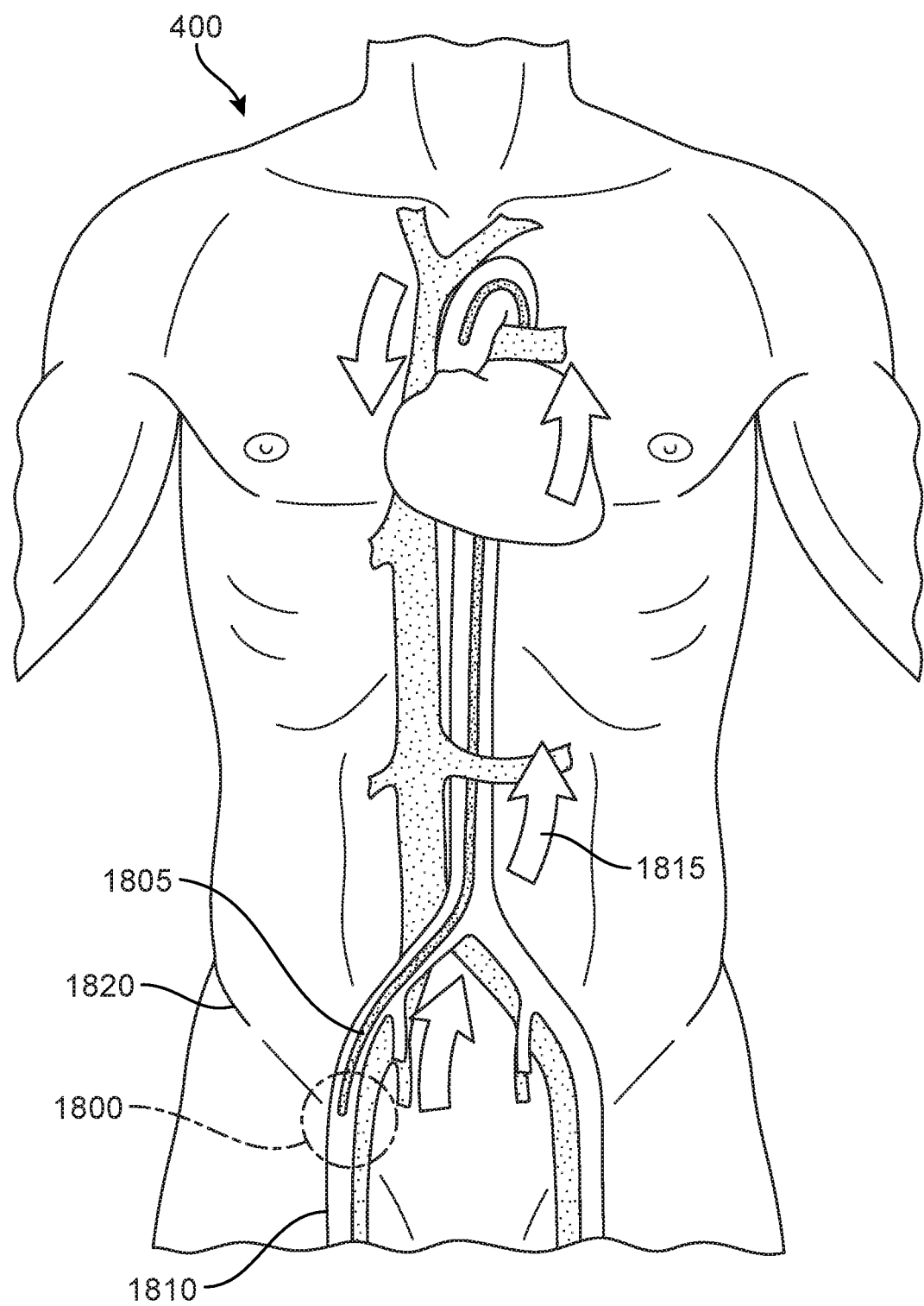
FIG. 18 is a schematic illustration of a femoral artery catheter insertion site.

In some embodiments, pressure bandages having similar property as the embodiments discussed above may be utilized for surgical sites that do not include a surgical pocket or an implanted device. One exemplary such surgical site is the femoral artery insertion site for cardiac catheters. FIG. 18 is a schematic illustration of a femoral artery catheter insertion site 1800. As shown in FIG. 18, a catheter 1805 may be inserted into a femoral artery 1805 in a generally superior direction indicated by an arrow 1815. As further shown in FIG. 18, insertion site 1800 falls approximately in the inguinal crease 1820 of the patient, which is the crease between the lower abdomen and the upper thigh regions of the patient.

Following catheterization procedures, after the catheter has been removed from the femoral artery, pressure must be held on the insertion site for a period of time to ensure that blood does not leak out of the hole made in the femoral artery into the surrounding tissue, which would cause a hematoma. In order to apply this pressure, various methods are typically used. In some cases, a doctor or nurse literally holds pressure with their own hand for twenty minutes or more. This is because the femoral artery insertion site for catheters is in a recess in the outer surface of the body and bandages do not apply a significant amount of pressure to the wound site.

The femoral artery insertion site for catheters is in the inguinal crease, which runs from the iliac crest of the pelvis to the pubic bone in the crotch of the patient. The inguinal crease is recessed below the surfaces of the abdomen and the upper thigh. Therefore, even a makeshift pressure dressing applied in this area would not apply much pressure to the insertion site. Therefore, the physician or nurse must apply the pressure by hand. Various types of devices have been developed to apply pressure in this location. But most are cumbersome, overly complicated, or generally ineffective. Because of the thickness and resilience of the pads used for the pressure bandages disclosed herein, pressure may be applied even in a recessed surgical site, such as the inguinal crease.

Figure 19:
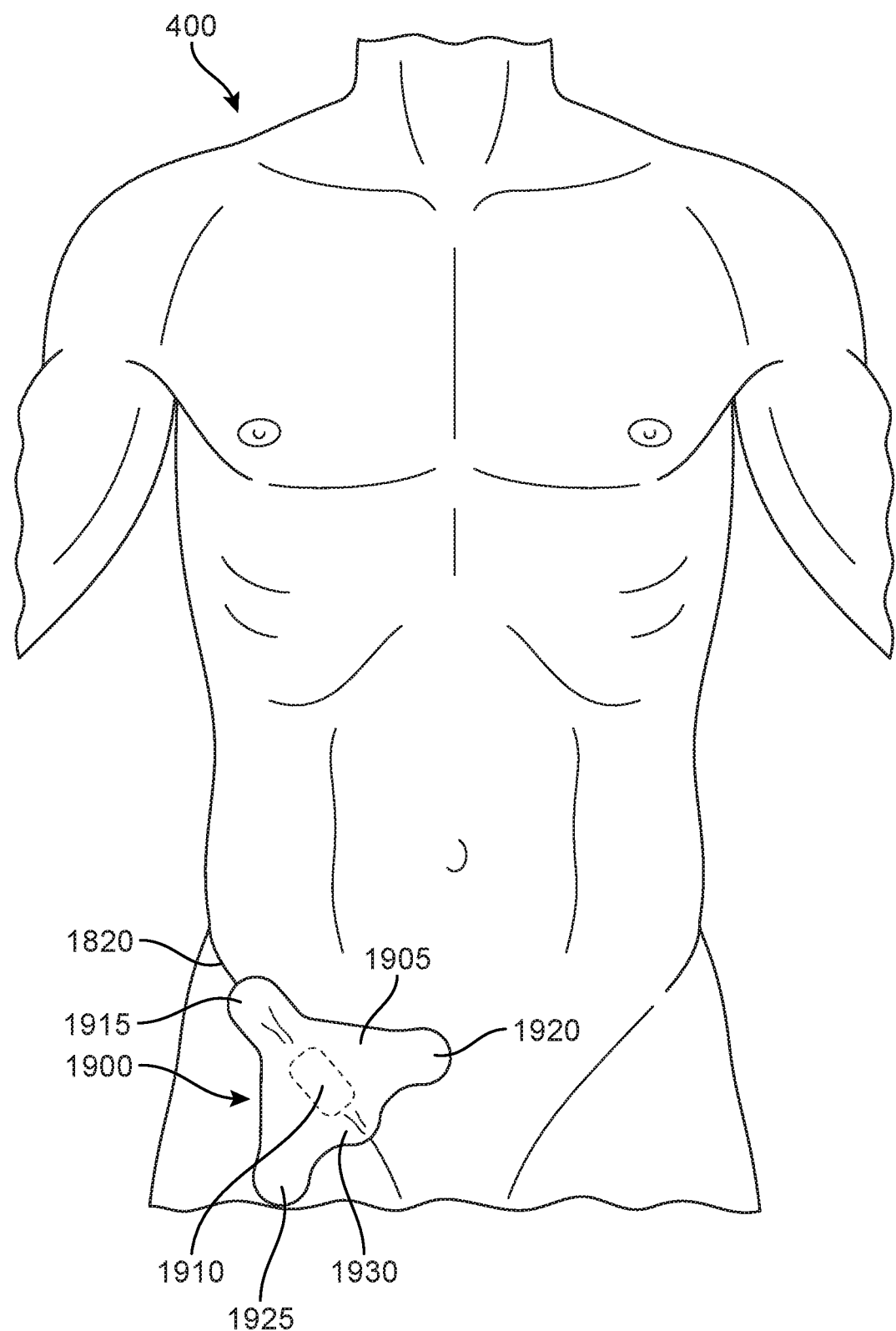
FIG. 19 is a schematic illustration of an embodiment of a pressure bandage applied to the femoral artery catheter insertion site shown in FIG. 18.

FIG. 19 is a schematic illustration of an embodiment of a pressure bandage applied to the femoral artery catheter insertion site shown in FIG. 18. As shown in FIG. 19, a pressure bandage 1900 may include an elastic sheet 1905 and a resilient pad 1910. The properties and characteristics of elastic sheet 1905 and resilient pad 1910 may be substantially similar to the corresponding components in the embodiments discussed above. For example, elastic sheet 1905 may have a substantially triangular shape. However, in some embodiments, resilient pad 1910 may have a substantially rectangular shape, which may be elongated in a direction along the inguinal crease. This elongated pad may facilitate the application of pressure into the recess of inguinal crease 1820.

The relative scale of pressure bandage 1900 may be generally smaller than that of the embodiments discussed above, simply due to the anatomical area being smaller than the lower abdominal, lower lumbar, and upper chest regions discussed above. Further, pressure bandage 1900 may employ a liner having cut lines to facilitate application of the bandage, as discussed above with respect to other disclosed embodiments.

In addition, pressure bandage 1900 may include a first anchor 1915, which may be configured to be applied with an orientation extending in a superior-lateral direction along inguinal crease 1820. Pressure bandage 1900 may also include a second anchor 1920 and a third anchor 1925 extending in generally opposite directions across inguinal crease 1820. In addition, pressure bandage 1900 may include a fourth anchor 1930 extending opposite first anchor 1915 in an inferior-medial direction. Depending on the patient's anatomy, in some cases, pressure bandage 1900 may be applied in an orientation that is 180 degrees from that shown in FIG. 19. That is, first anchor 1915 may extend in the inferior-medial direction along inguinal crease 1820 and fourth anchor 1930 may extend in the superior-lateral direction along inguinal crease 1820.

Figure 20:
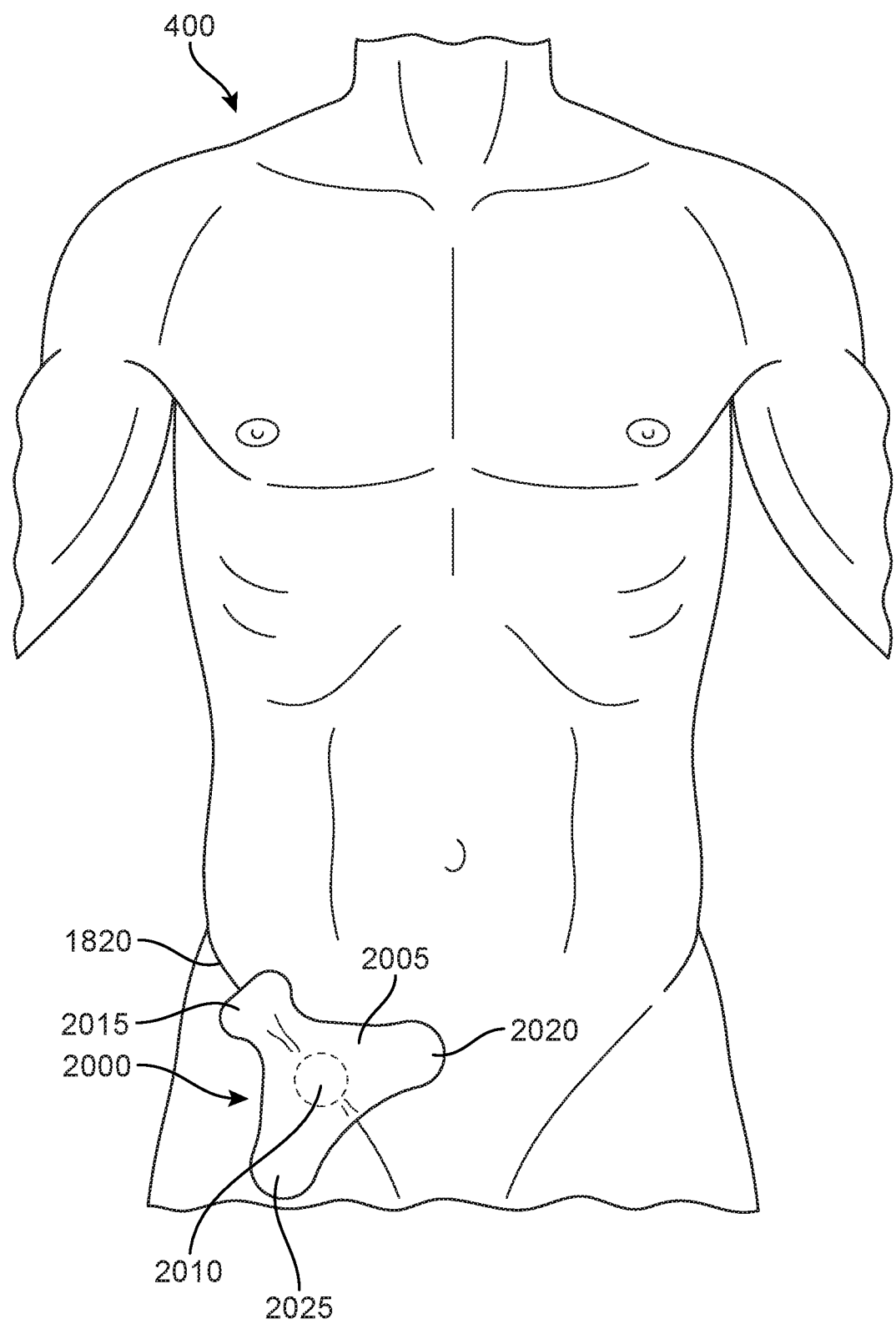
FIG. 20 is a schematic illustration of another embodiment of a pressure bandage applied to the femoral artery catheter insertion site shown in FIG. 18.

FIG. 20 is a schematic illustration of another embodiment of a pressure bandage applied to the femoral artery catheter insertion site shown in FIG. 18. In particular, FIG. 20 shows a pressure bandage 2000 including an elastic sheet 2005 and a resilient pad 2010. As shown in FIG. 20, elastic sheet 2010 may have a substantially similar configuration to elastic sheet 110 of pressure bandage 100 discussed above. For example, elastic sheet 2010 may have a substantially triangular shape and may include a widened first anchor 2015, a second anchor 2020, and a third anchor 2025. As shown in FIG. 20, in some embodiments, resilient pad 2010 may have a substantially circular shape. The substantially circular pad may facilitate applying pressure to a relatively small wound site consisting of a point at which an artery was punctured by a needle and through which a catheter was inserted and removed.

Figure 21:
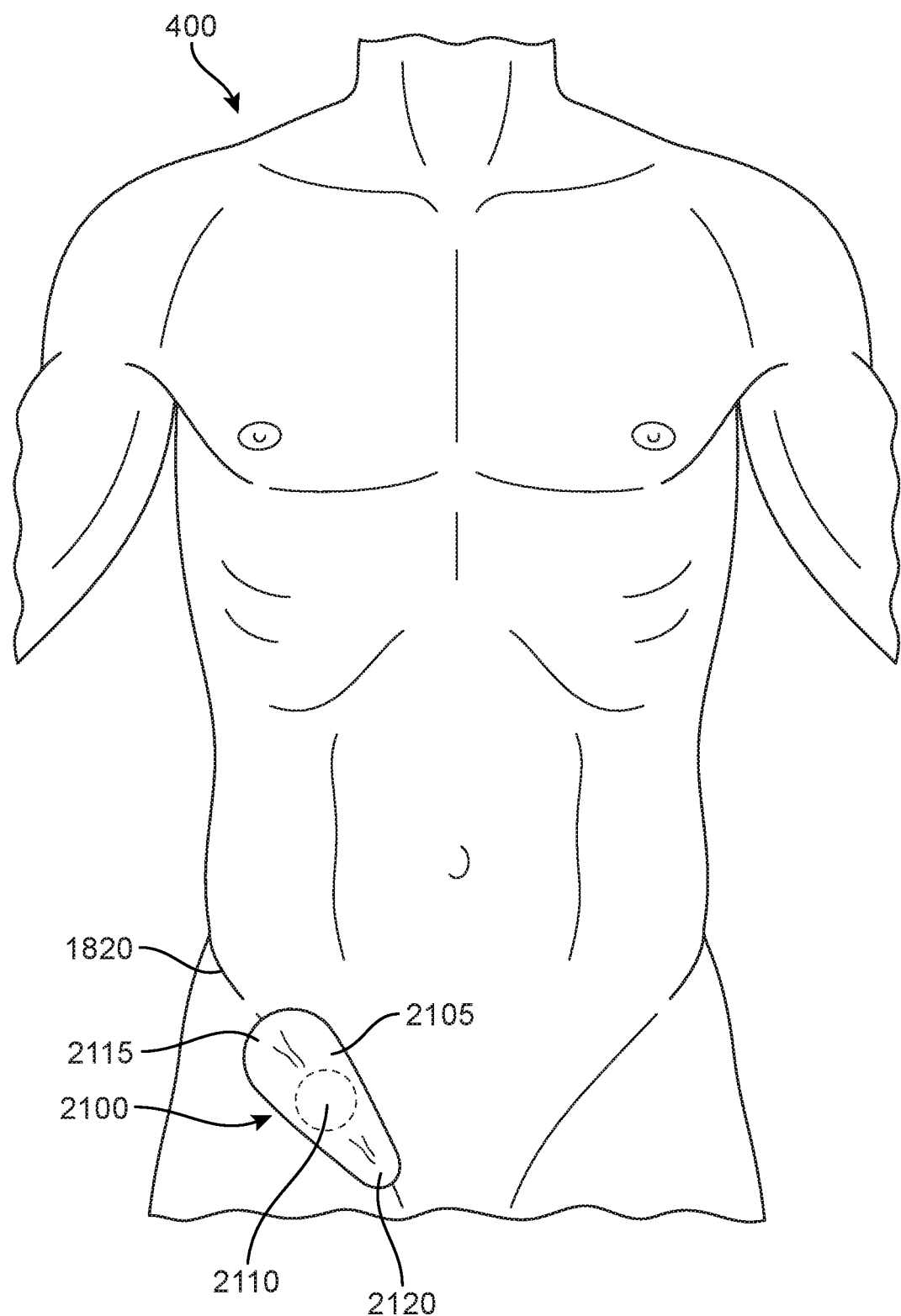
FIG. 21 is a schematic illustration of another embodiment of a pressure bandage applied to the femoral artery catheter insertion site shown in FIG. 18.

FIG. 21 is a schematic illustration of another embodiment of a pressure bandage applied to the femoral artery catheter insertion site shown in FIG. 18. As shown in FIG. 21, a pressure bandage 2100 may include an elastic sheet 2105 and a resilient pad 2110. Elastic sheet 2105 and resilient pad 2110 may have similar properties and characteristics as corresponding components in the embodiments discussed above. As shown in FIG. 21, resilient pad 2110 may have a substantially circular shape. Elastic sheet 2105 may have an elongate teardrop shape formed of a first anchor 2115 and a second anchor 2120. To form the elongate teardrop first anchor 2115 may be wider than second anchor 2120. The wider first anchor 2115 may facilitate fixation across inguinal crease 1820 in the upper region where the crease is not sharply creased, whereas the more slender second anchor 2120 may facilitate application to the lower portion of inguinal crease 1820, which is a much tighter area in which to apply a bandage.

Figure 22:
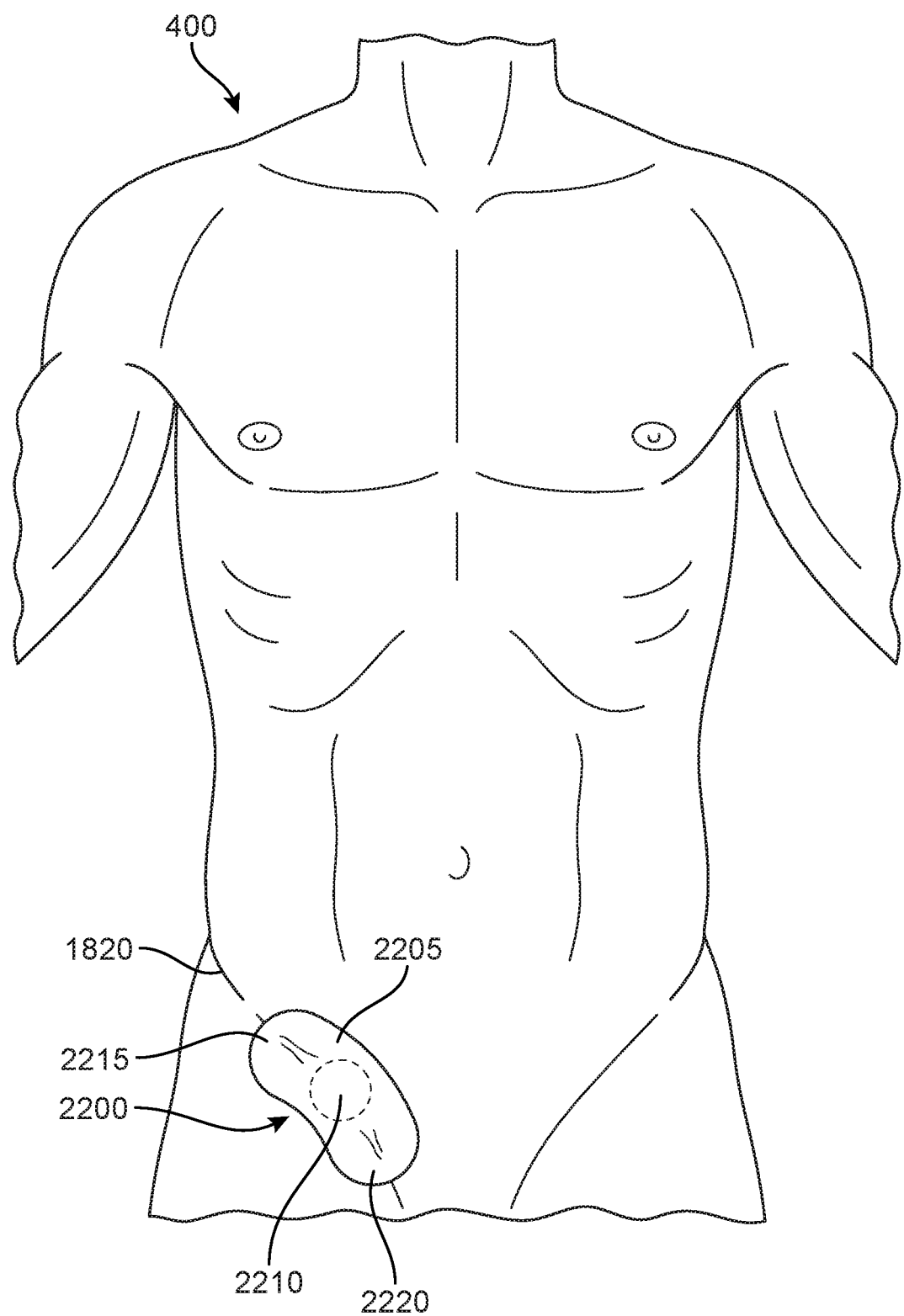
FIG. 22 is a schematic illustration of another embodiment of a pressure bandage applied to the femoral artery catheter insertion site shown in FIG. 18.

FIG. 22 is a schematic illustration of another embodiment of a pressure bandage applied to the femoral artery catheter insertion site shown in FIG. 18. As shown in FIG. 22, a pressure bandage 2200 may include an elastic sheet 2205 and a resilient pad 2210. Elastic sheet 2205 and resilient pad 2210 may have similar properties and characteristics as corresponding components in the embodiments discussed above. As shown in FIG. 22, resilient pad 2210 may have a substantially circular shape. Elastic sheet 2205 may have an elongate curved shape, such as a kidney bean shape, as shown in FIG. 22. At one end, elastic sheet 2205 may have a first anchor 2215. At the opposite end, elastic sheet 2205 may include a second anchor 2220. The curvature of elastic sheet 2205 may facilitate application to the insertion site for patients who have a substantially curved inguinal crease 1820. That is, the curvature of the kidney bean shape may better follow the curved contour of the upper leg. In some cases, a pressure bandage having the same or similar shape as shown in FIG. 22 may be used for cesarean-section (C-section) incisions. Such a kidney bean shape may be particularly suitable for curved C-section incisions, such as the Maylard incision and the Pfannenstiel incision.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A pressure bandage, comprising:
    an elastic sheet having a first coefficient of elasticity and an adhesive side;
    a resilient pad affixed to the adhesive side of the elastic sheet and having a second coefficient of elasticity;
    wherein the elastic sheet has a first predetermined shape that is configured to be applied to a corresponding anatomical location on the body of a patient; and
    wherein the first coefficient of elasticity and the second coefficient of elasticity are related such that, when the elastic sheet is stretched and adhered to the body of the patient, the resilient pad applies a predetermined amount of pressure to the body of the patient; and
    further including a liner affixed to the adhesive side of the elastic sheet and including a plurality of cut lines separating the liner into distinct sections, wherein the cut lines are configured to facilitate removing the distinct sections of the liner in a predetermined sequence and to form a pull tab upon partial removal of each of the distinct sections of the liner;
    wherein the plurality of cut lines are defined by abutting edges of the distinct sections of the liner;
    wherein the liner covers no portion of the resilient pad;
    wherein the elastic sheet is substantially triangular, including an outer perimeter having a first set of three sides;
    wherein the resilient pad is substantially triangular, including an outer perimeter having a second set of three sides, substantially corresponding respectively with the first set of three sides;
    wherein the plurality of cut lines between the distinct sections of the liner include three cut lines respectively extending from the second set of three sides of the outer perimeter of the resilient pad to the first set of three sides of the outer perimeter of the elastic sheet; and
    wherein the three cut lines are respectively located approximately at the midpoint of the respective sides of the resilient pad and elastic sheet.

2. The pressure bandage of claim 1, wherein the predetermined amount of pressure exerted by the pressure bandage when applied in the anatomical location on the body of the patient is in the range of approximately 5-30 mmHG.

3. The pressure bandage of claim 2, wherein the predetermined amount of pressure is in the range of approximately 10-25 mmHG.

4. The pressure bandage of claim 2, wherein the predetermined amount of pressure is in the range of approximately 15-20 mmHG.

5. The pressure bandage of claim 3, wherein the predetermined amount of pressure is in the range of approximately 5-15 mmHG.

6. The pressure bandage of claim 1, wherein the predetermined amount of pressure applied by the pressure bandage when applied to the anatomical location on the body of the patient reduces or eliminates blood flow in capillary vessels of the patient.

7. The pressure bandage of claim 1, wherein the predetermined amount of pressure exerted by the pressure bandage when applied in the anatomical location on the body of the patient applies a pressure against the patient's blood vessels in the anatomical location of at least approximately 8 mmHG.

8. The pressure bandage of claim 1, wherein the pressure bandage is configured to be applied to one or more of the following anatomical regions of a patient: an abdominal region, an upper chest region, a lumbar back region, and an inguinal crease region.

* * * * *